United States Patent [19]

Willeke

[11] Patent Number: 4,846,166

[45] Date of Patent: Jul. 11, 1989

[54] NON-INVASIVE QUANTITATIVE METHOD FOR FIT TESTING RESPIRATORS AND CORRESPONDING RESPIRATOR APPARATUS

[75] Inventor: Klaus Willeke, Cincinnati, Ohio

[73] Assignee: University of Cincinnati, Cincinnati, Ohio

[21] Appl. No.: 153,511

[22] Filed: Feb. 8, 1988

Related U.S. Application Data

[62] Division of Ser. No. 797,207, Nov. 12, 1985, abandoned.

[51] Int. Cl.[4] ............................................ A61M 11/00

[52] U.S. Cl. .......................... 128/200.24; 128/201.23; 128/202.13; 128/202.22; 128/206.24; 73/40

[58] Field of Search ...................... 128/202.13, 202.22, 128/205.23, 206.17, 206.24; 73/37, 37.9, 40, 49.2, 49.3, 52

[56] References Cited

U.S. PATENT DOCUMENTS

| | | | |
|---|---|---|---|
| 2,420,372 | 5/1947 | Heidbrink | 73/46 |
| 2,449,053 | 9/1948 | Burns et al. | 73/40 |
| 2,738,669 | 3/1952 | Silverman et al. | 73/40 |
| 3,486,366 | 12/1969 | Jackson | 73/46 |
| 3,580,051 | 5/1971 | Blevins | 73/40 |
| 4,146,025 | 3/1979 | Warncke et al. | 73/46 |
| 4,344,144 | 8/1982 | Damico et al. | 73/37 |
| 4,449,392 | 5/1984 | Huschke | 73/40 |
| 4,579,115 | 4/1982 | Wallroth et al. | 125/205.23 |
| 4,765,325 | 8/1988 | Crutchfield | 128/206.24 |

FOREIGN PATENT DOCUMENTS

| | | | |
|---|---|---|---|
| 613672 | 5/1935 | Fed. Rep. of Germany | 73/37 |
| 668011 | 11/1938 | Fed. Rep. of Germany | 73/40 |
| 705843 | 4/1941 | Fed. Rep. of Germany | 73/40 |
| 737593 | 6/1943 | Fed. Rep. of Germany | 73/46 |
| 698045 | 10/1946 | Fed. Rep. of Germany | 73/40 |

*Primary Examiner*—Max Hindenburg
*Assistant Examiner*—K. M. Reichle
*Attorney, Agent, or Firm*—Frost & Jacobs

[57] ABSTRACT

A method and apparatus for conducting the method is disclosed for non-invasive, quantitative respirator fit testing. The method includes the step of having the wearer properly position the respirator over his nose and mouth, inhale to create a negative pressure inside the respirator cavity volume, hold his breath and record the pressure differential versus time decay rate between the pressure inside the respirator cavity volume and that of the surrounding environment. The method may also include establishing a leakhole of known dimension, repeating the above steps and determining the volume of the respirator cavity based upon the results of the recorded differential pressure versus time by comparing the result to calibration curves.

The apparatus of the present invention includes modifying a conventional face mask respirator by providing the respirator with a pressure sensor and a leakhole of known dimension. Preferably, the apparatus can also include a calculator to continuously calculate a quantitative factor to indicate the degree of protection, which is based upon the volume of the respirator cavity divided by the volumetric flow rate through the leakhole or holes of unknown dimension and location for a standard unit of time, given an initial negative pressure in the respirator cavity.

10 Claims, 18 Drawing Sheets

BREATH HOLDING-LEAK TEST WITHOUT BODY OR FACE MOVEMENT. MSA COMFO HALF MASK-LARGE WITH 2 SEALED MSA TYPE H FILTERS, ONE OF THE FILTERS PROBED.

*EXPERIMENTAL DATA OF FIGURE 6 PLOTTED ON A LOGARITHMIC RESPONSE SCALE. RESPIRATOR TAKEN OFF BETWEEN RUNS. MSA COMFO HALF MASK LARGE.*

EXERCISING DURING BREATHHOLDING: SIDE TO SIDE MOVEMENTS MSA COMFO HALF MASK - LARGE.

*EXERCISING DURING BREATHHOLDING: UP AND DOWN MOVEMENTS. MSA COMFO HALF MASK-LARGE*

EXERCISING DURING BREATHHOLDING: OPEN AND CLOSE MOUTH WITHOUT INHALING.

LEAK HOLE EXPERIMENT WITH MSA COMFO HALF MASK-LARGE.

*ARTIFICIAL LEAK HOLE TEST OF FIG. 11 ON LOGARITHMIC RESPONSE PLOT.*

PRESSURE FIT TEST (FIG. 7) AND ARTIFICIAL LEAK HOLE TEST (FIG. 12) WHILE WEARING THE SAME RESPIRATOR, PLOTTED ON LINEAR-LOG PAPER.

STEADY BREATHHOLDING WITH WILLSON FULL FACE RESPIRATOR BM 1423. THE RESPIRATOR WAS REMOVED BETWEEN TESTS.

EXERCISING WHILE BREATHHOLDING: UP AND DOWN.
WILLSON FULL FACE RESPIRATOR BM1423

EXERCISING WHILE BREATHHOLDING: SIDE TO SIDE
WILLSON FULL FACE RESPIRATOR BM 1423.

EXERCISING WHILE BREATHHOLDING: OPENING AND CLOSING MOUTH. WILLSON FULL FACE RESPIRATOR BM 1423

LEAK HOLE EXPERIMENT WITH WILLSON FULL FACE RESPIRATOR BM 1423. ARTIFICIAL LEAK HOLE ABOUT 1.0 mm I.D.

EFFECT OF LEAKING THROUGH THE SAME HOLE INTO DIFFERENT RESPIRATOR CAVITY VOLUMES.

*VOLUME CALIBRATION OF KNOWN SPACES WITH ARTIFICIAL LEAK HOLES.*

NON-INVASIVE QUANTITATIVE METHOD FOR FIT TESTING RESPIRATORS AND CORRESPONDING RESPIRATOR APPARATUS

This is a division of application Ser. No. 06/797,207, filed Nov. 12, 1985, now abandoned.

BACKGROUND OF THE INVENTION

1. Field of the Invention.

The present invention relates to air purified respirators and a non-invasive, quantitative method for fit testing the respirator. In particular, the filtered air respirator is of the type having at least one filter for removing dust particles, for example, and/or chemical filters designed to remove chemical contaminants such as deleterious gases and particulates. Additionally, the present invention relates to air supplied respirators requiring a tight face seal between the respirator and the face of the wearer. Moreover, the present invention has utility as a respirator for filtering such substances as paint spray, smoke, dust, and military warfare agents. The invention also contemplates a preferred non-invasive quantitative method for fit testing respirators so that each respirator is fit tested to the end user, rather than the end user being fitted with a respirator which will be a model of the one to be employed.

2. Prior Art

There are basically four distinct types of respirator face mask configurations. The first type called the quarter-mask covers the mouth and nose, and the lower sealing surface of the mask is designed to be positioned between the user's chin and lower lip.

A second type of face mask respirator is called the "half-mask", which fits over the nose, around the user3 s mouth and under the user's chin. Half-masks generally seal more reliably than quarter-masks so that these type masks are preferred against more toxic materials. The quarter-masks are designed normally for use as dust respirators. The quarter-masks may also include air purifying elements or may be air supplied when employed in a toxic environment.

A third type of face mask respirator is the full face piece which covers roughly from the hairline to beneath the chin. This type of respirator offers better protection than the quarter-mask because it is capable of achieving a good seal around peripheral portions of the face which are not affected by such movements as breathing or talking. The full face respirator may include an air purifying element or may be air supplied. Additionally, this type of respirator may be used where eye protection is necessary because the purified air generally flows across the eyes of the user before it reaches the user's nose and mouth.

The fourth and last type of respirator configuration is the helmet-hood type, designed to fit over the entire head. This type includes a compressed air line which flows air to the interior of the helmet-hood. The air escapes from the helmet-hood type by percolating through and between the peripheral edge of the respirator. This type of respirator protects the head of the user, including the eyes because the helmet includes a transparent section which shields the eyes from hazardous agents. Generally, the compressed air is designed to first flow over and around the eyes of the user, and then flow downwardly to and around the mouth of the user. Excess air flowing through the helmet-hood and exhaled carbon dioxide are discharged from the helmet-hood area by flowing between the peripheral edge of the helmet-hood, or may be discharged with a conventional exhalation valve.

Each of the first three configurations of respirators generally includes one or more of the following: an air purifying element, for example, a pleated paper filter for particle removal or a chemical cartridge or canister for gas removal, an inhalation valve, and an exhalation valve.

The helmet-hood type generally does not include any of the above elements. Sometimes the helmet-hood type can include an air flow control valve to regulate the amount of air flowing into the helmet. The air can be supplied either by a positive pressure of compressed air or the air can be supplied on demand causing a slight negative pressure within the cavity volume. When the helmet-hood has a positive pressure with respect to the surrounding atmosphere, the supplied clean air forms a flowing, moving curtain which prevents dust, fumes, smoke, and chemical contaminants such as deleterious gases from flowing into the eyes and the breathing area. When air is supplied on demand to a helmet-hood type respirator, the respirator must fit tightly about the wearer to avoid drawing in air from the surrounding atmosphere.

Many different companies produce one or more of the four types of respirators. In fact, several million respirators are sold annually in the United States alone, to protect wearers from industrial and environmental contaminants. Additionally, recent concern about potential chemical warfare has motivated the military establishment to study new respirators for combat troops, and to study fit testing methods for the user of the actual respirator to be worn.

Because of the diversity in the dimensions of human faces, a single respirator cannot properly fit every person. Therefore, leaks between the respirator mask and the face are possible, particularly with the first three respirator configurations previously mentioned, thereby reducing the protection sought by the respirator. As a result, fit testing is necessary and, for many environments, legally required to determine which type, brand, and size of respirator will provide the necessary protection for the wearer. All the care that went into the designing and manufacturing of a respirator will not protect the wearer if there is an improper match between the face piece and wearer, or if improper wearing practices are employed. The latter problem may be cured by proper instruction. The former problem usually involves either quantitative or qualitative testing of several types of face mask respirators to determine the best fitting mask.

In a qualitative test, the wearer usually tests several respirators to determine which feels most comfortable and provides at least some protection through achieving a proper seal between the wearer and the respirator. In general, qualitative tests are usually fast, require no complicated, expensive equipment, and are easily performed in the field. The general disadvantages of qualitative tests are that such tests rely upon the wearer's subjective response, and thus are not entirely reliable. Moreover, a respirator that appears to fit properly during testing may not provide an adequate seal when the user grows a beard, gains weight or merely wears out the respirator, for example.

Qualitative fit tests approved by the U.S. Government and employed industrywide comprise the negative pressure test, the positive pressure test, the isoamyl acetate vpor (banana oil) test, and the irritant smoke test.

The negative pressure test consists of merely closing off the air inlet of the face mask. The air inlet is generally one or two cartridges or filters which are secured to the face mask typically by screw threads. The inlet or inlets are covered with the palms of one's hands so that no air can be drawn in through the air inlets of the mask. The tester inhales so that the face piece collapses slightly and holds his or her breath for about 10 seconds. If the face mask remains slightly collapsed and no inward leakage is detected, the respirator provides an adequate fit.

As stated previously, the subjective and non-quantitative nature of this simple test has severe drawbacks. For example, the pressure of one's palms on the filters or cartridges of the face mask would naturally cause the face mask to have a better seal around the wearer's face than normally occurs during use. Moreover, a slight deformation of the face mask may occur with a pressure of 10 to 20 centimeters of deflected water. Stronger deformation occurs at higer pressure differentials. However, normal breathing incurs a pressure of about 1 to 4 centimeters of deflected water. Consequently, the negative pressure test is employed under conditions which are not typically found in the working environment.

The positive pressure test is very similar to the negative pressure test and in general has the same advantages and disadvantages. The positive pressure test is conducted by closing off the exhalation valve of the face mask and exhaling gently into the face piece. The fit is considered to be satisfactory if a slight positive pressure can be built up inside the face piece without any evidence of outward leakage. Of course, the disadvantage of this test is again the subjective nature of the test. For example, the employees testing the face mask would not be exhaling at the same pressure. Thus, one employee may consider the mask satisfactory, while another employee may not. Moreover, a positive pressure is not normally incurred during the inhalation cycle of air purifying respirator usage.

The isoamyl acetate vapor test gives the user the opportunity to wear the face mask in a typical environmental atmosphere. Isoamyl acetate has a pleasant, easily detectable banana odor. The tester or wearer generally is positioned in an atmosphere or environment containing the isoamyl atmosphere. The face mask must include an organic vapor removing cartridge so that if the wearer or tester detects the smell of banana oil, the vapor is only due to the leakage between the wearer's face and the face mask. The atmosphere around the tester or wearer is created by saturating a piece of cotton cloth, for example, with the liquid isoamyl acetate and passing it close to the face mask near the sealing surface. Preferably, the entire test is conducted in a small booth or hood covering at least the wearer's head and shoulders. In such an enclosure, a concentration of the isoamyl acetate vapor of approximately 100 ppm is found to be adequate since most people can smell the vapor at concentration levels of about 1 to about 10 ppm. Initially, this test is conducted with the tester remaining perfectly still. If no banana odor is detected, then the test is expanded to include activities such as deep breathing, side-to-side movement of the head, up and down movement of the head, and talking loud enough to be understood by someone standing nearby. Such activities add to the dependability of the face mask since such movements often occur in the working environment.

One major drawback of the isoamyl acetate test is that the sense of smell is easily dulled and may deteriorate during testing to the extent that the wearer can only detect high vapor concentrations. Also, each individual differs from the others in the threshold detection limit, resulting in a satisfactory mask for some individuals and an unsatisfactory respirator for others, although the leakage is constant in all instances. Moreover, because isoamyl acetate has a pleasant smell, even at high concentrations, a wearer may subjectively state that the face mask fits comfortably without leakage, because of peer pressure to use a specific type mask or the comfort of the particular face mask.

The irritant smoke test is similar to the isoamyl acetate test in concept. However, instead of employing isoamyl acetate, which has a pleasant smell, an irritating aerosol produced by commercially available smoke tubes normally used to check the quality of ventilation systems is employed. Typically, the smoke tubes are filled with pumice impregnated with stannic chloride or titanium tetrachloride. When the seal of the tube is broken, the moisture in the air rects with the contents of the tube to produce a dense, highly irritating smoke consisting of hydrochloric acid. This test has a distinct advantage in that the tester reacts involuntarily to leakage by coughing or sneezing. Consequently, the likelihood of the tester or wearer giving a false indication of proper fit is greatly reduced. However, the aerosol produces extreme irritation because the hydrochloric acid tends to burn the sinus passages. Thus, great care must be exercised to avoid injury.

The irritant smoke test must be conducted in a hooded or enclosed environment where the tester initially remains stationary. If no irritating smoke is detected, the tester then proceeds to move his head from side to side, and again if no smoke is detected, to move his head up and down, and again if no smoke is detected, to talk loud enough to be understood by someone standing nearby. If the wearer still does not detect any irritating smoke, the face mask is judged to fit without excessive leakage.

A more precise way of determining the proper fit of a face mask is the quantitative test with test agents. The greatest advantage of quantitative testing with test agents is that the tests indicate face mask fit based upon a numerical number, which does not rely upon the subjective response of the wearer or tester. Such quantitative tests are employed most often when leakage must be minimized for work in highly toxic or harmful atmospheres such as nuclear radiation.

The disadvantage of quantitative fit testing with test agents is the expense of the testing equipment and the necessity of having highly trained personnel operate the equipment. Moreover, each face mask tested must be fitted with a test probe to allow sampling of the interior atmosphere of the face mask when it is properly worn. Consequently, the face mask used during testing is only a model of the face mask the tester or worker is to receive, instead of testing the actual face mask the worker is to use. Accordingly, minor nuances between the model tested and the actual face mask received could result in a poor or improper fit.

Recent studies of quantitative fit testing with test agents indicates that the position of the probe in the face mask may result in large discrepancies in the quantitative testing. The sampled agent concentration inside the face mask cavity depends on the location of the probe relative to the flow of purified air entering the respirator cavity, the location of the mouth or nose through which breathing occurs, and the location of the leak or leaks which is generally unknown. The mixing of agents inside the respirator cavity is incomplete during the generally short inhalation and exhalation periods. The measured concentration of the agent present may, therefore, not represent the true protection. This has been borne out by recent studies. See, Myer, W. R., *American Industrial Hygiene Association Journal,* Volume 45, No. 10, pages 681-688, 1984. For example, if the probe is positioned to the right side of the wearer's face, the results of quantitative testing with agents may not be the same as the results obtained when the probe is positioned at the left side of the face mask, or centered in the face mask. Because there is presently no standard for placement of the probe in the mask when testing, results obtained from one test cannot usually be correlated with results obtained from another test. Depending upon the location of the test probe and the location of the leak, the face mask may prove to be satisfactory in one instance and unsatisfactory in another instance. Consequently, while quantitative testing with test agents no longer relies on the subjective opinion of the wearer, it does possess certain disadvantages.

The presently employed quantitative tests measure the concentration of the test agent inside the mask cavity, i.e., between the mask and the face of the wearer, as compared to the atmosphere outside or surrounding the face mask. The types of quantitative testing conducted in industry and by the U.S. government comprise the sodium chloride test, DOP test (dioctylpthalate), the freon 12 test, and the sulfur hexafuoride test.

All presently employed quantitative testing involves placing the tester or wearer in an atmosphere containing easily detectable vapors or aerosols. Typically, the atmosphere is confined to a hood or an enclosure having a specified concentration of test agents contained therein. Leakage is expressed as a fit factor which is related to the concentration of the test agent in the atmosphere divided by the concentration of the test agent in the mask, when the mask is properly worn.

In the sodium chloride test, submicron size solid salt particles are dispersed by a nebulizer into a test chamber or hood. The penetration of the sodium chloride aerosol into the respirator is determined through a test probe inserted in the respirator and typically, the results are recorded on a strip chart. During testing, the wearer tests the face mask while remaining relatively stationary. Then, the wearer proceeds to move his head from side to side so that leakage from the work-simulated activity may also be recorded. Subsequently, the wearer oscillates his or her head up and down and then talks loud enough to be heard by one standing nearby. Test data from each of these movements for a given model of a face mask are compared against other models of face masks in order to determine the best face mask model fit. Comparison is made despite the inability to correlate results, as discussed previously.

The DOP test uses a dioctylpthalate aerosol in which the DOP particle is liquid, i.e., an oil. This test is similar to the sodium chloride test in that DOP particles are created by nebulization, for example, and are introduced into a flowing gas atmosphere in which the testing procedure described in the sodium chloride test are performed.

The freon 12 quantitative test is based upon a refrigerant gas—freon 12. However, this test is not often used because the presently available analyzing instrumentation has a very slow response time causing fluctuations in concentration of the refrigerant gas that penetrates the face mask. Again, testing procedures disclosed above are performed.

The fourth quantitative test mentioned above is based upon sulfur hexafluoride. Sulfur hexafluoride is a very stable gas and is one of the heaviest known gases having a density approximately five times that of air. The testing procedures disclosed above are performed.

In summary, the presently employed fit quantitative tests may comprise using a solid aerosol particle—the sodium chloride test; a liquid aerosol particle—the DOP test; a light refrigerant gas test—freon 12; or a heavy gas test—sulfur hexafluoride. As stated previously, the fit factor for the mask with any one of these test agents is given by or related to the concentration of the test agent in the environment divided by the concentration of the test agent within the face mask cavity.

In a presentation titled "Development And Validation Of A Simple Respirator Fit Test" by Miller which was presented at the Annual American Industrial Hygiene Conference in Las Vegas, Nev., May 19-24, 1985, Mr. Miller describes a method used by the Louisville, Ky., Metropolitan Sewer District, which he modified. In this modified method, a manometer is connected to the face mask and is observed during testing. The testing procedure calls for a worker or tester to properly don a respirator face mask, and during a period in which the tester or worker is holding his or her breath, the manometer is observed. If, after several seconds, the pressure is substantially reduced, the face mask fails the test. On the other hand, if the pressure level is not substantially reduced, the respirator passes the test. Consequently, :his method involves measuring a pressure change with time as the basis for failing or passing the fitness of a face mask or respirator.

The disadvantage of the Miller method is simply that it does not take into consideration the volume of the face mask. In other words, if the cavity between the face mask and the worker is large, and has a small leak, the face mask may easily pass the pressure versus time judgment described by Mr. Miller. On the other hand, if the face mask is a quarter size face mask, for example, and has the same total volume leakage as the full face mask, it may not pass the pressure change versus time judgment. Thus, while both face masks have the same leakage, one passes the test because it has a large face mask cavity, while the other smaller face mask fails the test because of its small face mask cavity. Another disadvantage of the Miller method is that it does not relate the rate of pressure change in the mask to a specific quantitative leak rate.

In summary, the prior art devices are inadequate to obtain a consistent fitness between a worker and a face mask that is reliable. The qualitative tests have the disadvantage that the fitness of a particular face mask is based upon subjective responses of the wearer. Moreover, the isoamyl acetate and the irritant smoke tests cannot be conducted each and every time the wearer employs the mask. With the quantitative tests, the test results are inaccurate and cannot be correlated between one test and another. Moreover, the wearer only tests a model of the actual face mask he is to use. Lastly, all the quantitative tests are very expensive. With the Miller method, the test procedure does not factor into consideration the respirator cavity volume, nor does it render a numerical fit factor. Accordingly, none of the prior art tests is satisfactory for indicating a numerical value which reliably indicates the fit of a mask on a person's face. Consequently, a need exists for a method which is inexpensive, can be quickly conducted and overcomes the problems of the prior art methods. Moreover, new embodiments for a face mask are needed which would achieve the above method and enable the wearer to test the face mask each and every time the wearer enters a highly toxic atmosphere.

SUMMARY OF THE INVENTION

The present invention includes a new procedure or process by which the degree of fit, and thereby protection, of the face mask or respirator is measured when the respirator is worn by a wearer or other human being. Because of the diversity in the dimensions of human faces, a single respirator cannot properly fit every person. Therefore, leaks between the respirator mask and the face are possible, thereby reducing the person's protection. Consequently, fit testing is necessary and, for many environments, fit testing is a legal requirement to determine the type and size of face mask or respirator which will provide the necessary protection for the wearer.

The present invention concerns a method for non-invasive fit testing face masks that is quick, reliable, inexpensive and offers quantitative results. Additionally, the present invention concerns a face mask designed to carry out the above method and designed to enable the wearer to test the face mask before each entry into a hazardous air environment.

One of the steps of the present invention is preparing a series of correlation graphs in which various known volumes of gas having the same or different negative pressure are permitted to equalize through a leakhole of a specific size. The graphs or charts plot the rate at which the pressure changes with time for the different volumes selected. The larger the cavity volume, the slower the pressure difference will decrease for a given leakhole. Consequently, the slopes of the pressure decay curves relate to known volumes. Once these charts are prepared, the basic non-invasive quantitative fit test method of the present invention can be quickly conducted.

In this invention, the leakage is measured indirectly. Since the leakage is at unknown locations, the leak rate cannot be measured directly. If the wearer inhales and then holds his or her breath while the respirator cavity is held at a negative pressure, the pressure change with time in the respirator cavity will depend on the leakage rate into the cavity. The potential contaminants enter the respirator cavity in that leakage flow. The leakage flow rate thus determines the degree of protection or the lack of it. Since pressure equilibrates almost instantly, in contrast to gas or particle mixing inside the cavity, the pressure can be monitored anywhere in the respirator cavity, irrespective of the random leak location or locations. The pressure change inside the cavity depends on the volumetric leak flow into the cavity and the respirator cavity volume itself. The cavity volume will therefore be measured as well while the respirator is worn by the wearer. The volumetric inflow of outside air, relative to the respirator cavity volume, is therefore a measure of the protection provided.

In the broadest sense, the method of the present invention comprises positioning a face mask respirator onto the wearer or worker, who will be the end user of the face mask; having the wearer inhale to achieve a negative pressure in the respirator cavity of several centimeters or inches of water (preferably the negative pressure will not exceed a value at which the respirator significantly deforms); having the wearer hold his or her breath and measuring the pressure change with time. At the end of this first portion of the test, the wearer can resume normal breathing. This first portion of the test can be repeated several times with the wearer remaining motionless. Additional tests would also include exercises such as the conventional side-to-side head movement and the up and down head movement. When opening and closing the mouth, which would simulate talking, the wearer holds his or her breath. Once the above procedures have been conducted, the second part of the test may be performed. The second part of the test includes determining the face mask cavity volume between the face of the wearer and the inside of the face mask. The second portion of the method includes positioning the face mask on the wearer, if the mask is not already so positioned; having the wearer inhale to create a negative pressure inside the cavity volume; opening an orifice of a specific known size and plotting or recording the pressure change versus time. The slope of this curve indicates the leakage through the known orifice and through the unknown holes. The method includes subtracting the slope of the graph obtained from leakage through the unknown hole from the slope of the graph obtained from leakage through the known plus unknown holes to achieve a slope indicating the respirator cavity volume. However, generally the leakage through the known size orifice is many times larger than the total of all the unknown leakages. When this situation exists, it is not necessary to subtract the unknown leakages since they are minor. Accordingly, only the slope of the graph of the known and unknown leakages is employed. This slope can be compared to the pressure decay slopes from the correlation charts or graphs. The cavity volume of the respirator can be determined by selecting the pressure decay slope which most closely approximates the slope graph of the leakages. Reading the volume of the selected pressure decay slope yields the cavity volume of the face mask.

Lastly, the degree of fit of the face mask respirator can be quantified as will be discussed later. Quantifying the degree of fit permits comparison between different respirators so that the best fit for the wearer can be achieved.

In the broadest sense, the present invention also includes respirator apparatus in which the face mask or respirator includes a leakhole of known size which is capable of being opened or closed, a pressure sensor capable of recording the pressure in the respirator cavity volume, and an analog or a digital readout of the pressure. Preferably, the face mask of the present invention will include a test canister having a digital readout and a specific size leakhole which can be opened or closed. The canister can replace the normal air purifying canister employed on the face mask. Accordingly, when it is time to check the degree of fitness of the face mask before entering the working environment, the worker merely switches canisters and tests the fit of the mask. This can be done without the worker removing the face mask. When the test is complete, the test canister will be replaced by the air purifying canister.

The present invention will be more fully understood and described with reference to the following drawings and complete description.

In an air-supplied respirator, a valve closes the air supply. A pressure sensor and a leak hole as described above are built into the face mask or into the supply hose downstream of the valve, or are attached through an opening to the face mask or supply hose.

DESCRIPTION OF THE PREFERRED EMBODIMENTS

Figure 2:
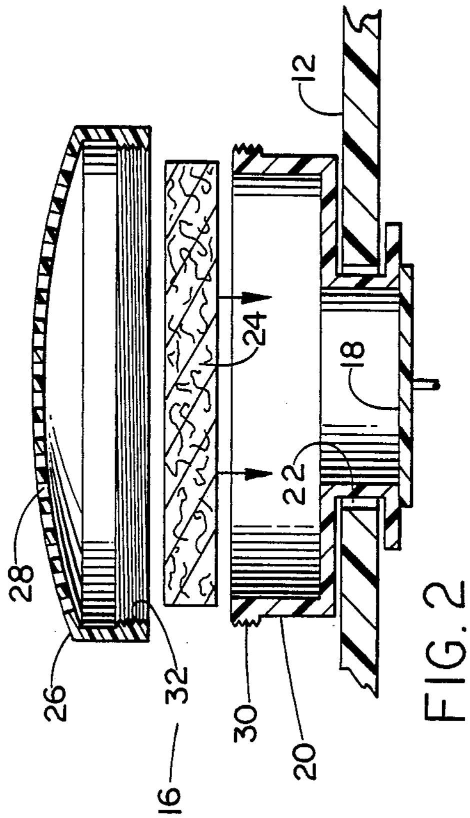
FIG. 2 is an exploded, fragmentary cross-sectional side view of a conventional filter canister.

The non-invasive quantitative respirator fit test described herein is suitable for air purifying respirators, atmosphere supplying respirators, and any other respirators which require a seal between the respirator or face mask and the wearer's face.

The present invention is applicable to any size face mask or respirator, for example, the quarter mask, the half-mask, the full face mask, or a full hood or helmet type mask, or any other face mask which covers at least the person's mouth or nose.

In the present procedure, the leakage of the face mask during fit testing is measured indirectly. Since the leakage occurs at one or more unknown locations, the leak rate cannot be measured directly. If the wearer inhales and holds his or her breath, while the respirator cavity is held at a negative pressure, the pressure change with time in the respirator cavity will depend upon the leakage rate into the cavity. The potential contaminants or hazardous agents that are present in the air environment enter the respirator cavity through leakage flows. The leakage flow rate thus determines the degree of protection or lack thereof. Since pressure equilibrates almost instantly, the pressure can be monitored anywhere in the respirator cavity by a sensor positioned within or near the cavity, irrespective of the random leakage locations. The rate of pressure change inside the cavity depends upon the volumetric leakage flow rate into the cavity and the respirator cavity volume itself. The cavity volume will therefore be measured while the respirator is being worn by the wearer. This is essential because facial features which project into the interior of the respirator cavity change the volume of the respirator cavity, when worn.

Whenever air leaks into the respirator during the negative pressure created by inhaling, the pressure decreases from initial pressure $P_1$ in the mask at time $t_1$, to pressure $P_2$ at time $t_2$. For a constant leak, the logarithmic decrement per linear time interval is constant.

There is defined WLS=Willeke Leak Slope $$WLS = \text{Willeke Leak Slope} = \frac{\text{Ln } P_1 - \text{Ln } P_2}{t_2 - t_1} = \frac{\text{Ln } P_1/P_2}{t_2 - t_1} \quad (1)$$

Where P is the pressure difference between ambient pressure and the pressure inside the respirator cavity. The units for WLS are (1/time), e.g. (1/sec). The initial pressure $P_1$ should be larger than 1 cm $H_2O$ at time $t_1$, preferably between 5 and 10 cm $H_2O$. Pressure $P_2$ is recorded after breath holding for 10 to 60 seconds, preferably for about 20 seconds. Any exercise should be initiated after time $t_1$ and terminated before time $t_2$, the head position and facial feature at time $t_2$ being the same as at time $t_1$. The slope by WLS, equation 1, is an indication of the respirator fit. A small WLS indicates a good fit, a large WLS indicates a bad fit, WLS=O indicates a perfect fit.

There is further defined $$WFF = \text{Willeke Fit Factor} \quad (2)$$

$$\frac{1}{WLS \times t} = \frac{1}{\frac{\text{LN } P_1/P_2}{t_2 - t_1} \times t}$$

where t is the time of breath holding, between 10 to 60 seconds. The WFF for a leaking respirator depends on the value of t. A value of t≐20 seconds is recommended for the definition of WFF. The value of WFF is nondimensional. A small value of WFF represents a bad respirator fit, a large value of WFF represents a good respirator fit.

WFF=(infinity) for no leakage.

If the time defined for the WFF is the same as the time at which $P_1$ and $P_2$ were recorded, e.g. 20 sec, then $$WFF = \frac{1}{\text{Ln } P_1/P_2} \quad (3)$$

There is further defined $$WRV = \text{Willeke Respirator Volume} \quad (4)$$

as found by the artificial hole test described in the present invention. The unit of WRV is given in $cm^3$, for example.

The WLS is proportional to the volume of air leaking into the respirator cavity per unit time per unit volume of respirator cavity. Multiplication of WLS by WRV is therefore proportional to the volumetric leak rate into the respirator cavity. There is defined:

$$\begin{aligned} WLR &= \text{Willeke Leak Rate} \\ &= WLS \times WRV \end{aligned} \quad (5)$$

The units of WLR is volume per time, e.g. $cm^3/sec$. The actual volume of air leakage into the respirator cavity per unit time, $Q_{leak}$ is given by $$Q_{leak} = K \times WLR \,. \quad (6)$$

Where coefficient K is a function of the pressure differential inside the mask while the wearer inhales, and a function of the gas/air medium properties, such as temperature, viscosity, density and absolute pressure. The value of K may be determined theoretically or experimentally.

During inhalation, the volumetric air flow rate through the air purifying elements or through the supply hose is $$Q_{inhalation} = \text{volume of air per unit time during inhalation} \quad (7)$$

There is now defined:

$$WPN = \text{Willeke Protection Number} = \quad (8)$$

$$\frac{Q_{inhalation}}{Q_{leak}} = \frac{Q_{inhalation}}{K \times WLR}$$

This non-dimensional number gives the ratio of purified air flow rate to leak rate during inhalation and as such is a measure of protection of the wearer's breathing space.

Figure 1:
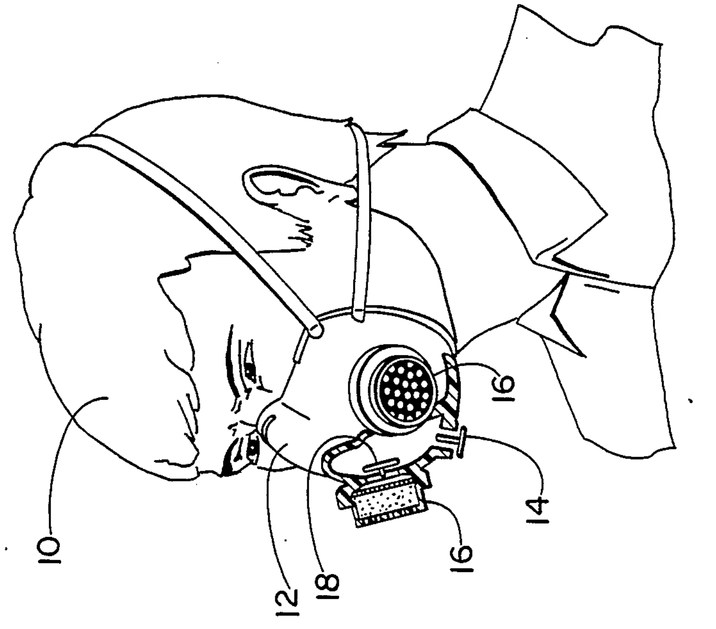
FIG. 1 illustrates a fragmentary perspective view of a half-mask respirator as it is worn by the user.

In the particular device illustrated in FIG. 1, reference numeral 10 designates a typical wearer who works or moves in a hazardous air environment such as a carcinogenic environment, a nuclear radioactive environment, or a military action environment. The wearer has a half-mask 12 which covers entirely his nose, mouth and chin. The half-mask 12 includes an exhaust valve 14 and a pair of filter canisters 16 which act as air purifying elements, and are positioned over the inhalation valve 18, as is conventionally known in the art.

In keeping with the invention, the filter canister or air purifying element 16, illustrated in FIG. 2, includes a bottom portion 20 which is securely attached to the face mask 12 through an opening 22. Abutting against the bottom portion 20 of the air purifying element 16 is the inhalation valve 18. A filter element 24 is positioned within the lower or bottom portion 20 and is designed to reasonably seal itself to the bottom portion 20 so that air must flow through the filter element 24. The air purifying element 16 also includes a cap 26 having a plurality of orifices 28 which permit air to be drawn therethrough to the filter element 24. The cap 26 can be secured to the bottom portion 20 in any means desired, such as by mating screw threads 30 and 32, as illustrated in FIG. 2. Other types of air purifying elements are known in the art and the particular type employed does not distinguish the present invention, that is, the present invention is designed to operate with any type of air purifying element for face or respirator masks.

Figure 4:
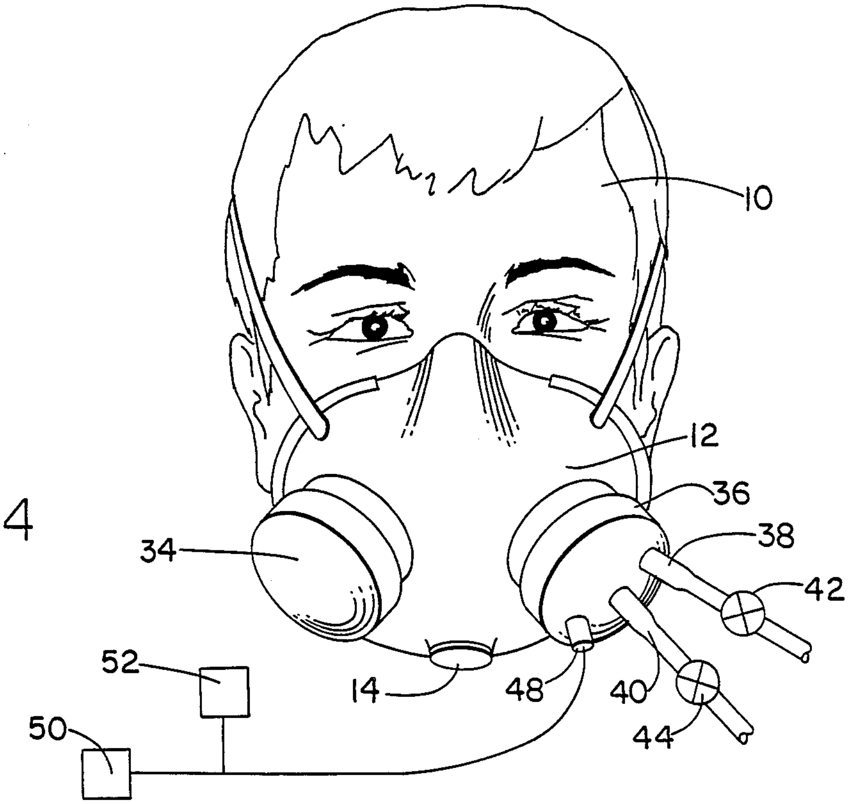
FIG. 4 is a frontal view of a half-mask, including the improvements of the present invention, as it is worn by the user.

FIG. 4 illustrates a half-mask correctly positioned on a wearer 10 which includes substitute filter canisters or elements for the purpose of carrying out the method of the present invention to fit test the face mask or respirator 12 to the wearer 10. In particular, the filter element 16, illustrated in FIGS. 1 and 2, have been replaced by a capped filter canister 34 and a testing canister 36, as will be explained more fully later.

The capped filter canister 34 comprises a bottom portion 20 such as that illustrated in FIG. 2. However, the upper portion 26 has been replaced with a portion which has no openings like those illustrated by reference numeral 28 in FIG. 2. In other words, when the upper portion of the capped filter canister 34 is securely fastened to the lower portion, no air can flow into or out of the face mask through the capped filter canister 34. Preferably the interior volume of canister 34 is completely sealed rather than just omitting opening 28, so that the interior volume of the canister is not added to the volume of the respirator cavity.

As stated previously, filter canisters can comprise a plurality of different types and shapes. The capped filter canister illustrated in FIG. 4 is to illustrate the form of the present invention, but is not intended to limit the present invention to any specific type of filter canister. Any conventionally known filter canister can be sealed in any typical manner, such as by sealing the openings with an adhesive, or the like, so long as the sealed filter canister no longer permits air to flow into or out of the respirator cavity volume.

Figure 3:
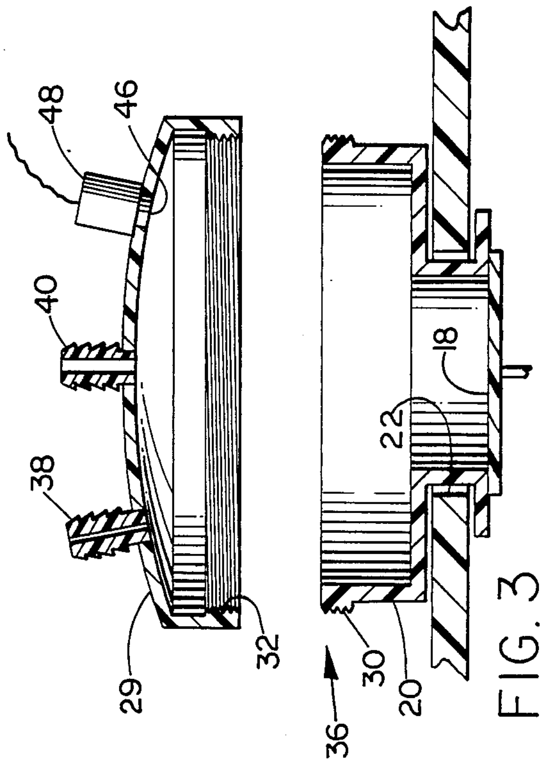
FIG. 3 is an exploded, fragmentary cross-sectional side view of a test canister of the present invention.

The test canister 36 illustrated in FIG. 3 is designed to replace the second air purifying element 16 in a conventional face mask. Where the conventional face mask only includes one air purifying element, the air purifying element is designed to be replaced with a test canister 36. In such an instance, there is no need for the capped filter canister 34.

The test canister 36 includes a bottom portion such as that illustrated by reference numeral 20 in FIG. 3. The top portion 29 attaches to the bottom portion 20 in the same manner as the conventional cap 26. The top portion 29 of the test canister 36 includes two inlets 38 and 40, each having an open-close valve 42, 44, respectively, as illustrated in FIG. 4. Inlet 38 is of a known dimension, for example, 1.0 mm ID. Inlet 40, on the other hand, serves as a normal breathing inlet for the face mask or respirator. The valves 42 and 44 can be any type so long as they can be quickly actuated to the fully open and fully closed position.

The test canister 36, as illustrated in FIG. 3, includes a third inlet 46 which is in communication with a pressure sensor and monitor 48. Preferably, the pressure sensor and monitor 48 has attached to its output port a strip chart recorder 50 and a digital calculator and indicator 52. The strip chart recorder 50 can be any conventionally known type of linear or logarithmic strip chart recorder so long as the recorder is capable of recording the sensed pressure from the pressure sensor and monitor 48 over a period of time. The digital calculator and indicator 52 can be any type which is capable of indicating the instant pressure the sensor and monitor 48 is instantaneously detecting and additionally, capable of calculating a quantitative value for the WPN.

Although FIG. 3 illustrates a test canister 36 having three inlets 38, 40 and 46, the filter mask or respirator 12 could optionally contain the three inlets sealably formed or molded in the face mask or respirator at the time of manufacturing. Likewise, the pressure sensor and monitor 48 could be mounted on the face mask 12. In such an instance, all the conventional air purifying elements 16 that accompany a conventional respirator or face mask, can be replaced or otherwise sealed in any manner desired so that the respirator can be fit tested by employing the inlets which are molded within the face mask itself. Additionally, some inlets could be provided on a testing canister and some inlets could be molded within the face mask during manufacturing. It would also be within the scope of the present invention to merely have one inlet of a known dimension which would serve as the normal breathing inlet and which has secured thereto a pressure sensor and monitor. In such an instance, the known dimension must be sufficiently large to permit normal breathing, and yet be limited (in size) to how quickly pressure uniformly equilibrates. In other words, if the known dimension is too large, the pressure in the respirator cavity may not be uniform during fast air flow into the respirator cavity. The preferred embodiment is to have separate inlets because the normal breathing inlet should be many times larger than the leakhole of known dimension in order to permit the pressure sensor and monitor 48 to accurately sense the pressure with respect to a designated time duration. If only one inlet is employed, the pressure sensor and monitor 48 must be extremely quick and accurate in sensing the pressure because a large inlet equilibrates the pressure between the reservoir cavity volume and the environment outside the respirator much quicker than a very small inlet of known dimension.

Figure 5:
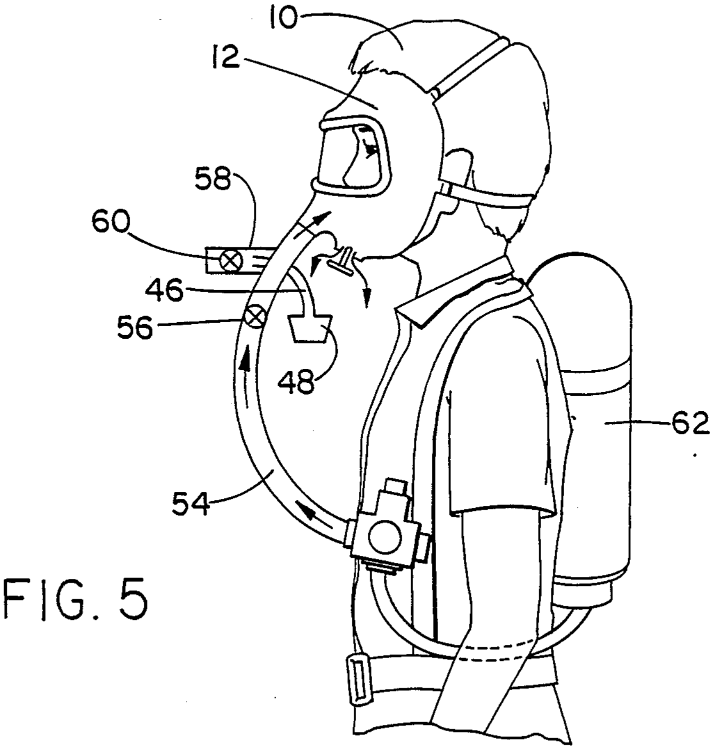
FIG. 5 is a side view of a full-mask respirator with the atmosphere supplied on demand, including the improvements of the present invention.

Illustrated in FIG. 5 is a full face mask 12 correctly positioned on a wearer 10, which includes an air supply tube 54 having an open-close valve 56 positioned therein and an inlet 58 to serve as a leakhole having a known dimension. The inlet 58 includes a valve 60 designed to be quickly actuated to the fully open or fully closed position. Also in communication with the air supply tube 54 is an inlet 46 which is pneumatically coupled with a pressure sensor monitor 48, as previously described. The air tube 54 can be connected to a conventional air tank 62, for example, or to any other source of air, such as an air compressor.

When a full face mask is employed, such as illustrated in FIG. 5, the conventional air supply tube can be replaced with a test air supply tube 54, or the air supply tube 54 can be manufactured so as to always include valves 56 and 60, along with inlets 46 and 58 and the pressure sensor monitor 48. Additionally, the full face mask 12 could include any or all of these elements, which could be molded into the face mask at the time of manufacture.

Before the non-invasive quantitative respirator fit test of the present invention is initiated, the wearer breathes normally through the unobstructed opening represented by reference numeral 40 in FIG. 3, for example. The test is initiated by closing the breathing inlet 40 by closing the valve 44 manually, by a solenoid or by some other actuator mechanism. At the time of initiating the test, the valve 42 is also in the closed position so that no outside air is drawn in through test canister 36. The respirator wearer inhales to achieve a negative pressure in the respirator cavity of several centimeters or inches of water. Preferably, the negative pressure should not exceed a value at which the respirator deforms significantly and appreciably changes the respirator cavity volume. Having obtained a desired pressure level inside the cavity, the wearer holds his or her breath or otherwise stops breathing through his nose and mouth. Optionally, the nose should be closed by a nose clip to avoid involuntary breathing.

All movements of the face should be avoided except during prescribed exercising. Movements of the face change the volume of the respirator cavity and consequently, the measured pressure. Therefore, at the beginning, during, and at the end of each pressure test, the facial contour should be the same with prescribed exercising deformation permitted only during certain tests.

The pressure inside the cavity is measured during the entire test by a dynamic pressure sensor 48 whose response can be recorded by analog or digital signals, recorded on a strip chart, for example. Optionally, both the strip chart and pressure sensor can be mounted on the face mask respirator. At the end of the pressure test, the breathing inlet is opened again, and the wearer resumes normal breathing. The test can be repeated several times so as to achieve consistency in the result.

Several types of tests can be performed. The basic test is one in which the wearer remains motionless. Additional tests would include prescribed exercises such as the conventional side-to-side head movements and the up and down head movements. The pressure can also be recorded while opening and closing the mouth without breathing movements, etc. Before and after each exercise, the person being tested should resume the same facial setting while the pressure in the cavity is being sensed. At the end of each test or test sequence, the wearer may take off the respirator being tested. However, preferably the tester will leave the respirator in place while performing the various tests or exercises.

If no air leaks into the respirator cavity are detected, the pressure in the cavity remains constant during the breath holding duration. The slope of the pressure decay curve determines the quality of fit. The faster the pressure decreases, the larger the leak. A steady leak flow during breath holding without facial movement will result in a smooth decay curve. If the respirator does not deform, i.e., if the respirator cavity volume does not change, the pressure difference between the inside and outside of the cavity follows an exponential decay curve, i.e., the pressure remaining in the cavity decreases to the same fraction of its value after each successive equal time interval. When the results of the experimental decay curve are plotted on a log-linear plot, with the pressure on the logarithmic scale and the time on the linear scale, a straight line results with the slope as an indicator of the rate of pressure decay. During exercising and/or during unsteady leakage, the pressure curve will show diverse results and the fit of the face mask or respirator is given by the slope of the curve on the linear-log plot before and after the unsteady leakage, when the facial contours are the same. Logarithmic amplification of the pressure signal will facilitate the numerical determination of the slope value.

In many instances, it may be desirable to prop open or pull out the inhalation valves to avoid opening and closing of these valves during slight twitching of the facial surfaces.

For the purposes of determining the respirator cavity volume, the following procedure is conducted. Given a leakhole of a specific size, the rate at which the pressure changes depends on the volume of the respirator cavity. The larger the cavity volume, the slower the pressure difference will decrease for a given leakhole, e.g., the volume of the respirator cavity is generally much larger for a full face respirator than for a half mask. Therefore, the slope of the pressure decay curve should be related to the volume of the respirator cavity to determine the volumetric rate of leakage. Assuming, for example, a rigid circular leakhole of known dimension, the exact amount of air entering the respirator cavity can be calculated from the knowledge of the pressure decay with time and the volume of the space into which the air leaks. Conversely, knowledge of the respirator cavity volume and the pressure change due to the leakage, determines the leak rate. Therefore, the volume of the respirator cavity should be determinable when the volume of the respirator cavity volume is expected to deviate from an expected value for a specific respirator.

Conceptually, the easiest way to measure the volume of the respirator cavity is to fill that volume with water or some other liquid while all valves are closed, with the respirator worn by the wearer or by a dummy. However, a dummy must have the exact facial features of the wearer in order to produce a fit factor which is specific to that wearer. Additionally, filling the respirator cavity volume with water while the mask is being worn by the wearer has obvious disadvantages. For example, water could seep into the wearer's nose and thus include a volume not designed to be included in the respirator cavity volume measurement.

The present method described herein involves the same dynamic pressure sensor 48, or a similar one with a faster response time, than is employed for the face seal test, previously described. An artificially small hole of known size or dimension provides leakage into the respirator or mask. The hole and a corresponding valve can be built into the respirator or into a test canister which is an accessory with the respirator.

At the initiation of the leakage test, the leakhole 38 is manually opened or actuated by some other mechanism. As illustrated in FIGS. 3 and 4, the inlet 38 is a leakhole of known dimension with an open-close valve 42. The wearer then inhales to a given negative pressure level and holds his or her breath while the recording device records the pressure decay curve given by air leakage through the leakhole of known dimension and through any unknown leakages. This can be repeated several times while the artificial leakhole is open and the normal breathing inlet is closed. For a fixed leak hole size, the slope of the decay curve is a unique function of the volume in the respirator cavity, if no other leak occurs. By making this artificial leakhole much larger than the total of all leakages, the pressure decay with the artificial hole is much faster than during the breath holding test. Thus, as a good approximation, the unknown leaks can be assumed not to affect the leakhole test for volume determination. If necessary, calibrated graphs, equations or computer programs can be made, which give the respirator volume cavity for the measured pressure decay curve with the leakhole.

The calibrated graphs, for example, can be prepared by leaking air into rigid spaces of known volume through the same size leakhole and monitoring the pressure decay rate with a pressure sensor. The sensor must be fast enough to correspond to the fast pressure decay. Therefore, it may, be necessary to use a separate sensor with a faster response time than the one employed during the regular pressure test. A series of tests with different volumes will result in a variety of pressure decay slopes. By comparing the pressure decay slope of the specific mask being tested with the series of various pressure decay slopes, the volume of the respirator cavity can be determined.

The described pressure test of the present invention is quantitative, and is an inexpensive alternative to conventional fit testing with aerosols. The pressure test of the present invention does not require the generation of an aerosol cloud in an enclosure, nor is it invasive. It does not require puncturing of the mask for a probe. Since the pressure can be sensed anywhere in the respirator cavity, or in an accessory, such as in the air purifying element or air supply hose, this non-invasive technique permits quantitative fit testing of the actual respirator to be worn. It is also ideally suited for a quick check performed by the wearer with the actual respirator before entering a hazardous air environment.

EXPERIMENTAL EXAMPLE 1

In this experiment, a half mask from MSA (Mine Safety Appliances Company), Comfo model with two Type H filters was employed. The filter material of the Type H filters was removed and one of the filter canisters was sealed by packing the canister with clay and using an epoxy adhesive to seal the exposed peripheral surfaces. In the remaining filter canister, the filter material was removed and three small metal tubes were fitted within the filter canister and the canister was sealed so that no other opening in the canister existed.

One of the openings was a leakhole of known dimension which had an off-on valve attached thereto; another of the openings was a large normal breathing inlet with an on-off valve attached thereto, and the third opening served to pneumatically connect a pressure sensor monitor to the face mask to determine the interior pressure during testing. Attached to the pressure sensor monitor was a magnehelic pressure gauge by Dwyer Company capable of registering pressures in the range of 0–10 cm of water. The pressure sensor was a Valedyne model MC1-3 and incorporated therewith was a pressure transducer Valedyne model DP45. An oscilloscope (B & K Precision Model 1474) was connected to the demodulator and a strip chart made by Honeywell Model Electronik No. 194 was employed to record the pressure variations.

The mask was worn under ordinary working conditions. All tests were performed with a clip on the nose of the tester. No grease or petroleum jelly was used to improve the fit, i.e., the mask was dry and the wearer's face was dry. All breath holding tests were performed at 5 seconds/inch on the strip chart. All artificial leakhole tests were performed at 1 second/inch on the strip chart. The valve for the normal breathing tube was open and the valve for the leakhole of known dimensions was closed.

The specific steps for this respirator fit test were as follows: Once the wearer was breathing normally with the face mask properly positioned, he closed the valve on the normal breathing inlet and inhaled to achieve an initially negative pressure in the respirator cavity of a few centimeters or inches of water. The pressure was monitored by the dynamic pressure sensor and the pressure change with time was recorded by the strip chart recorder. The wearer held his breath for approximately 20 to 25 seconds so that the pressure change with time would be recorded at different differential pressure levels. In Test A, as set forth in FIG. *6a*, the differential pressure was quite high. In Test B, the differential pressure was of lesser strength than in Test A, as shown in FIG. *6b*. In Test C, the differential pressure was small and less than the pressure of Test B as shown in FIG. *6c*. As illustrated in FIGS. *6a*, *6b* and *6c*, the results of each test illustrate a uniform exponential decay rate with time. Once the negative pressure within the respirator cavity is substantially reduced, the test may be terminated. 1

Figure 6C:
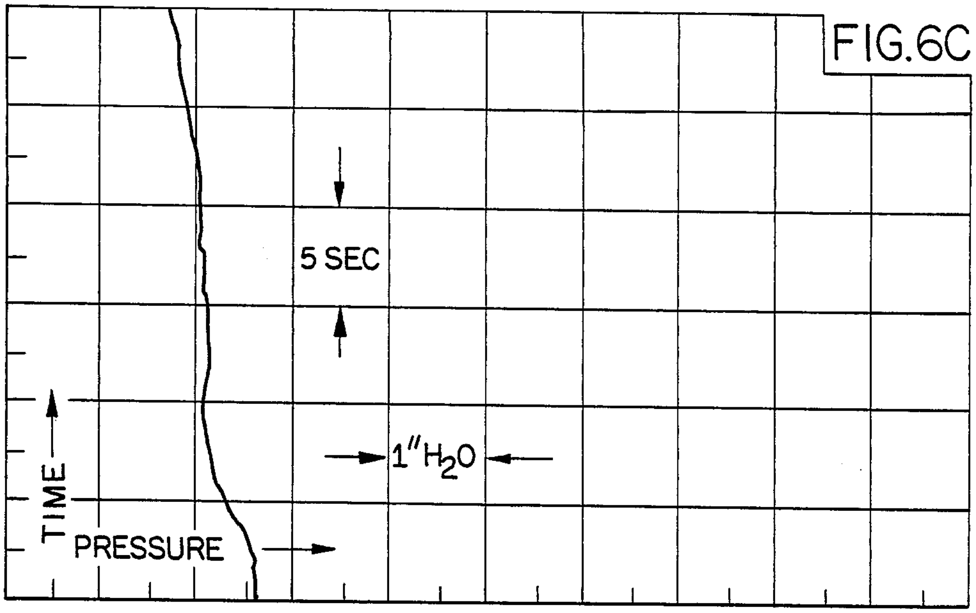
FIGS. 6*a*, 6*b* and 6*c* are strip chart graphs of pressure versus time illustrating three different breath-holding tests without body or face movement obtained with a half mask respirator. The inches of water deflection are proportional to the negative pressure in the respirator cavity.
Figure 6B:
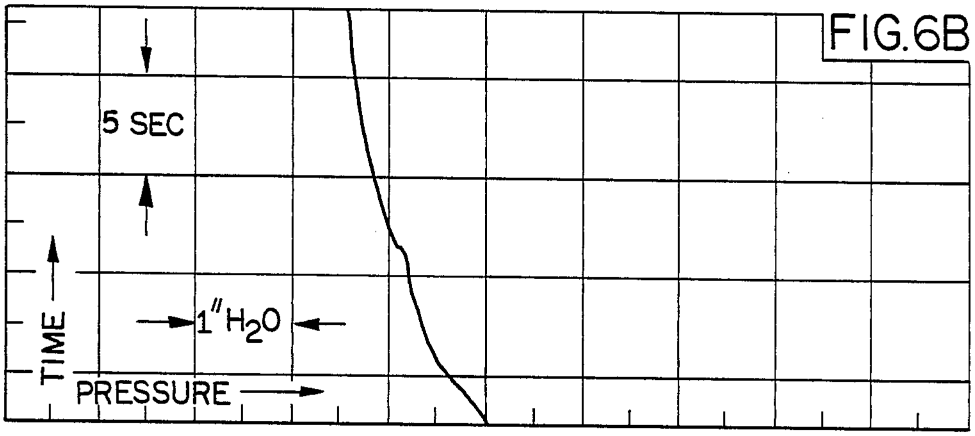
Figure 6A:
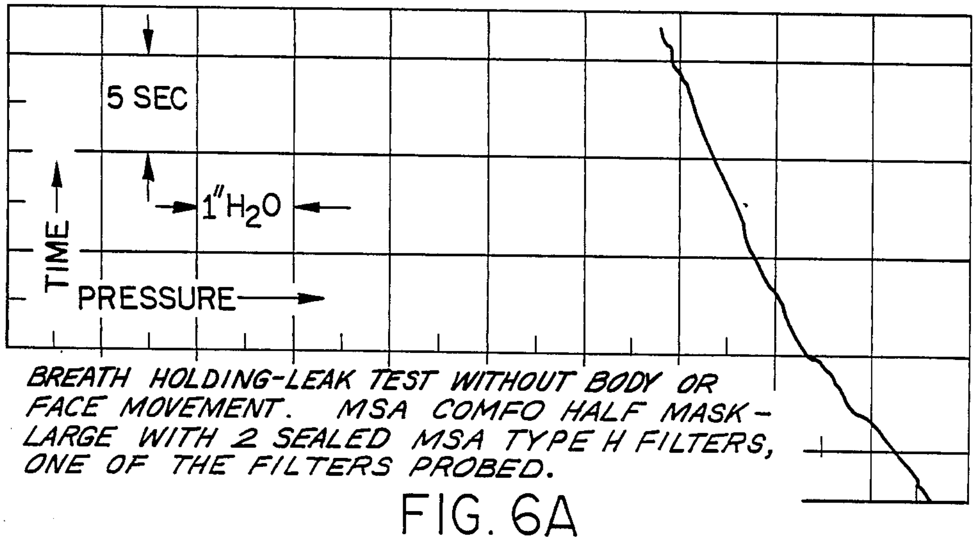

Typical Values from FIG. 6 for Half Mask Respirator

FIG. 6a:

$$WLS = \frac{\text{Ln } P_1/P_2}{t_2 - t_1} = \frac{\text{Ln } 9.7/7.15}{20 \text{ sec}} = \frac{0.31}{20 \text{ sec}}$$

$$= 1.53 \times 10^{-2}/\text{sec} = 0.0153/\text{sec}$$

$$WFF = \frac{1}{\text{LN } P_1/P_2} = 3.28$$

if $WRV = 100 \text{ cm}^3$:

$$WLR = WLS \times WRV = \frac{0.0153}{\text{sec}} \times 100 \text{ cm}^3 = \frac{1.53 \text{ cm}^3}{\text{sec}}$$

if $WRV = 200 \text{ cm}^3$:

$$WLR = 3.06 \text{ cm}^3/\text{sec}$$

FIG. 6c:

-continued $$WLS = \frac{\text{Ln } 2.6/1.93}{20 \text{ sec}} = \frac{\text{Ln } 1.35}{20 \text{ sec}} = 1.55 \times 10^{-2}/\text{sec}$$

$$= 0.0155/\text{sec}$$

$$WFF = \frac{1}{\text{LN } 1.35} = 3.36$$

or $$WLS = \frac{\text{LN } 2.61/1.68}{30 \text{ sec}} = 1.46 \times 10^{-2}/\text{sec} = 0.0146/\text{sec}$$

if $WRV = 100 \text{ cm}^3$:

$$WLR = WLS \times WRV = \frac{0.0155}{\text{sec}} \times 100 \text{ cm}^3 = \frac{1.55 \text{ cm}^3}{\text{sec}}$$

if $WRV = 200 \text{ cm}^3$:

$$WLR = 3.1 \text{ cm}^3/\text{sec}$$

Figure 7:
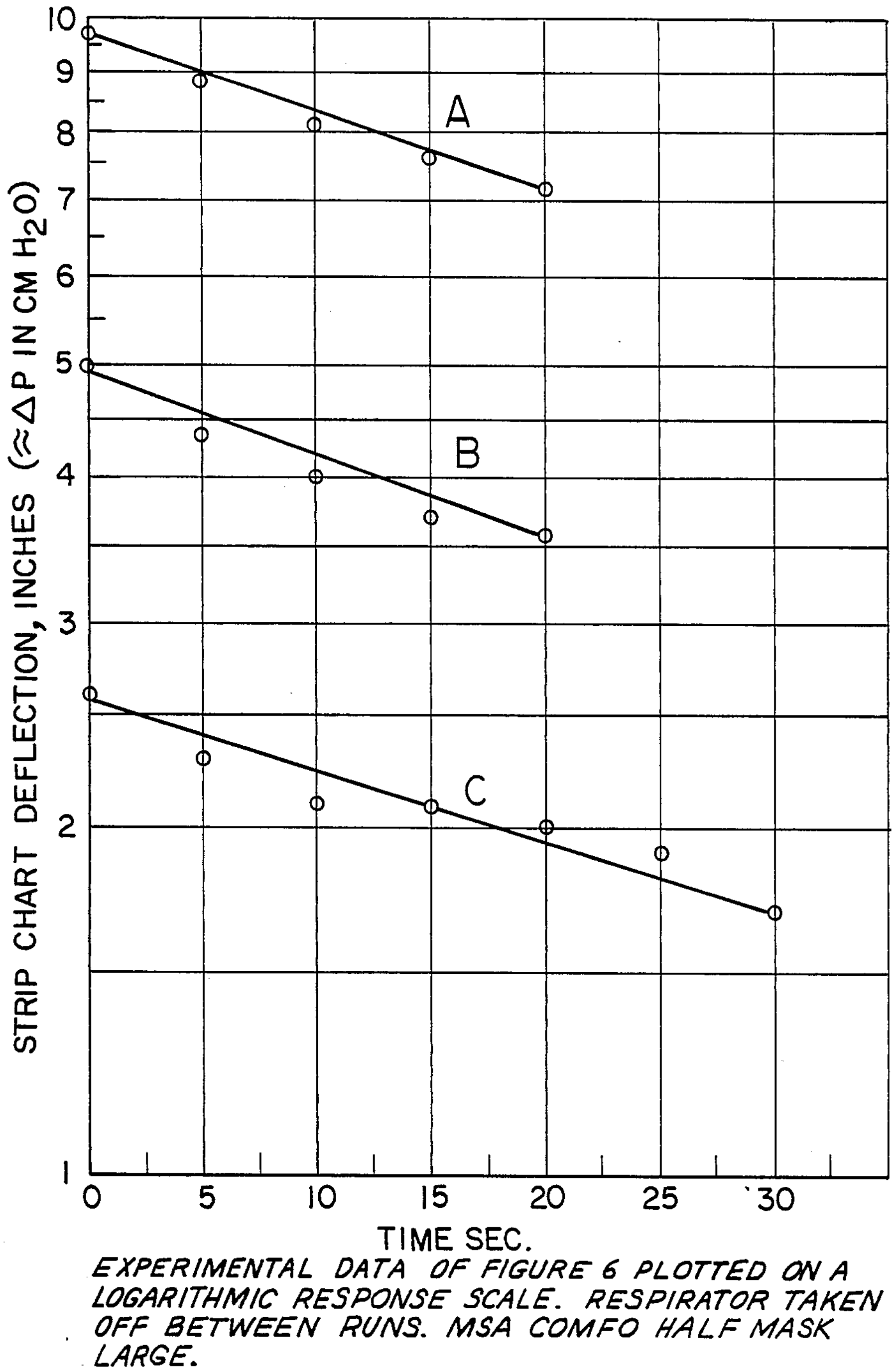
FIG. 7 is a log-linear plot of the pressure versus time for the three tests conducted in FIGS. 6*a*, 6*b* and 6*c* with pressure being plotted on the logarithmic scale.
Figure 8B:
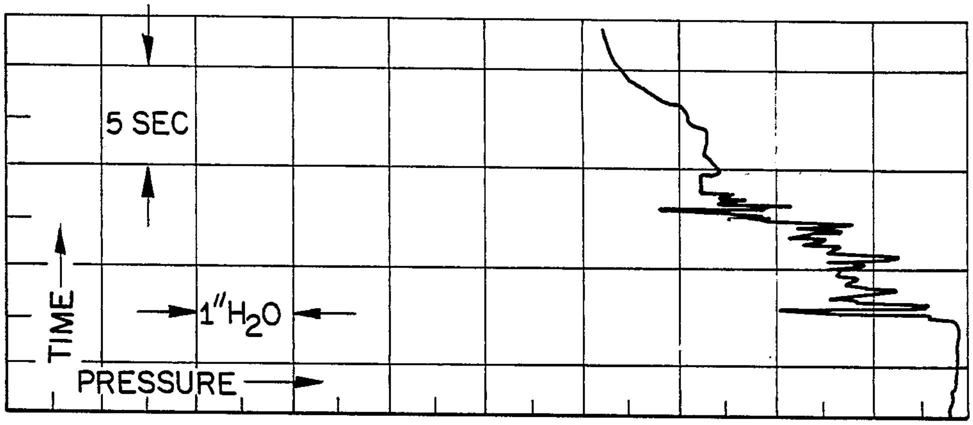
FIGS. 8*a* and 8*b*. are graphs of pressure versus time during two breath-holding tests using a half mask respirator while conducting side-to-side head movements.
Figure 8A:
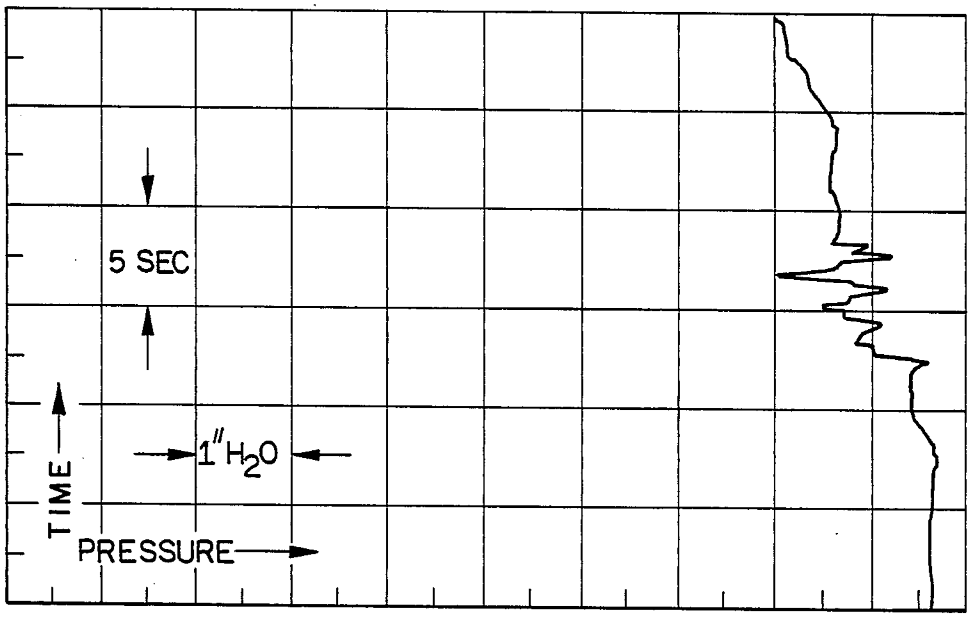
Figure 9B:
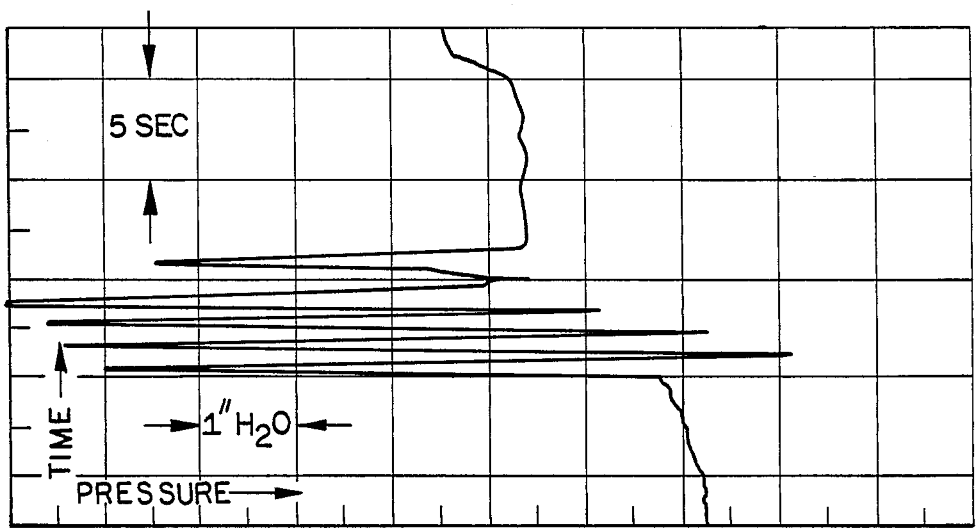
FIGS. 9*a* and 9*b* are graphs of pressure versus time during two breath-holding tests using a half mask while conducting up and down head movements.
Figure 9A:
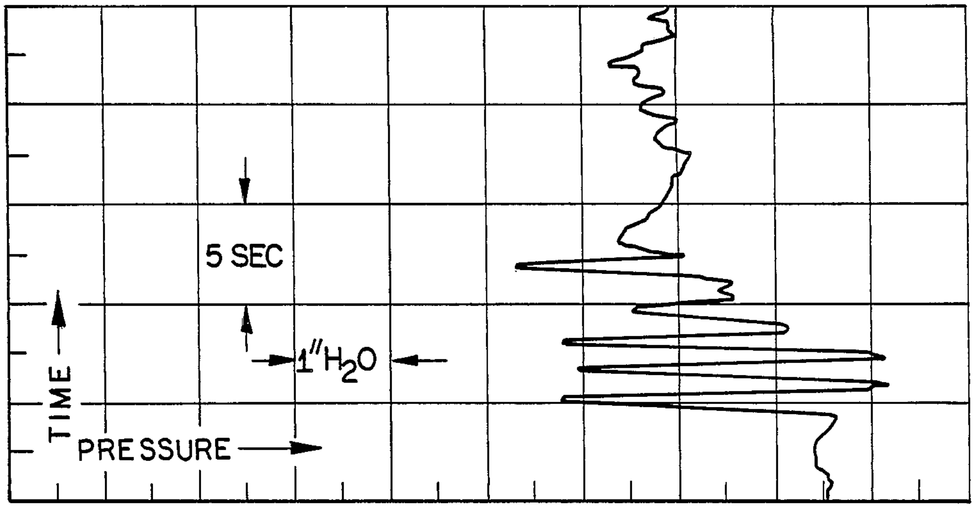

In FIG. 7, the pressure differential versus time was charted on a log-linear scale with the pressure differential being on the log scale. In each experiment, Tests A, B and C indicated approximately the same decay rate, that is, each log-linear plot of curve A, B and C has approximately the same slope.

EXPERIMENTAL EXAMPLE 2

In Example 1, the tester held his head and facial features steady so as to not affect the interior respirator cavity volume. In this experiment, the same equipment and face mask were employed and the tester again held his breath, but now moved his head side-to-side during the 20 to 25 seconds of breath holding, as illustrated in FIGS. *8a* and *8b*. Note that in both Test A and B, the initial seal was almost perfect, that is, little if any pressure was lost before the side-to-side head movement. However, the side-to-side movement dislodged the respirator, resulting in instantaneous leaks which were recorded by the strip chart as a drop in pressure. Although the strip chart recorded a series of peaks and valleys, pressure can only decrease as a result of leakage. It is theorized that the peaks, which represent an increase in pressure are due to slight decrease in respirator cavity volume during movement. The difference in pressure after the cessation of all movement is due to leakage. In Test A, near the end of the breath holding test where the side-to-side movement was terminated, the mask substantially resealed itself so that the decay rate was steady and much less than that which occurred during the side-to-side head movement. In Test B, the face mask did not reseal i:self and the leakage rate continued even after cessation of all movement. The results of Tests A and B are illustrated in FIGS. *8a* and *8b*.

EXPERIMENTAL EXAMPLE 3

The next experiment conducted was the breath holding test with up and down head movement. The results of this test are illustrated in FIGS. *9a* and *9b* in which two separate Tests A and B were conducted. In both Tests A and B, the initial pressure differential was substantially at a steady state decay rate. Then, the up and down head movement began and these movements were recorded on the strip chart as very steep peaks and valleys. It is theorized that these peaks and valleys are primarily the result of either differential pressure excursions caused by distortions in the Tygon tubing during the up and down movement, or facial deformations below the chin, for example. These distortions would not occur as strongly if the pressure sensor was directly attached to the mask since there is no need for Tygon tubing. In such an instance, one would only see differential pressure excursions due to volume changes in the respirator cavity volume or due to leaks in the face mask. Near the end of each Experiment A and B, the up and down head movement was terminated and the pressure differential decay rate resumed a more steady and uniform decay rate, particularly in Test B.

EXPERIMENTAL EXAMPLE 4

Figure 10B:
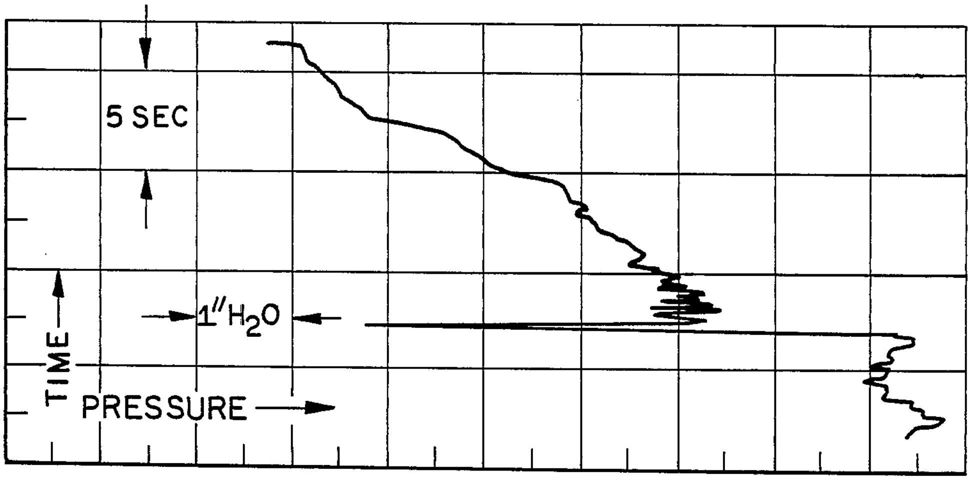
FIGS. 10*a* and 10*b* are graphs of pressure versus time during two breath-holding tests using a half mask while conducting open and close mouth movements without inhaling.
Figure 10A:
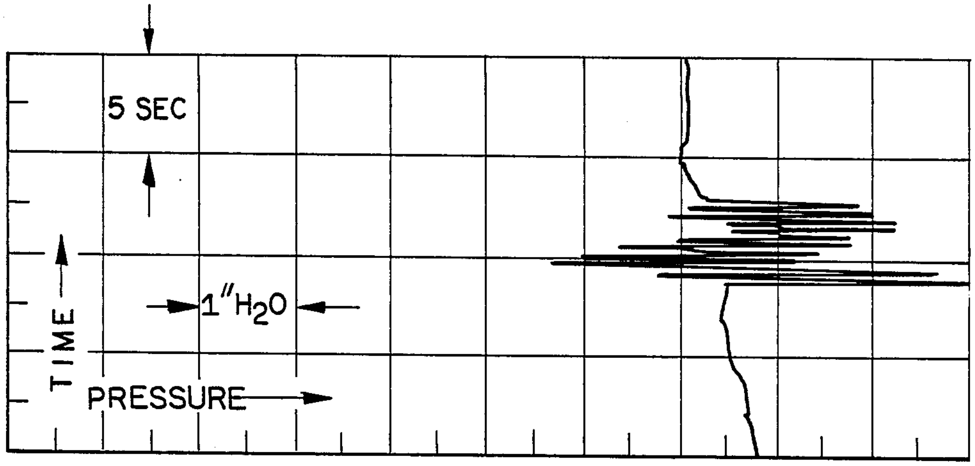

The equipment used in this Example was the same as that used in Example 1. In this Example, the experiment was conducted during the breath holding test in which the mouth was opened and closed without inhaling or exhaling. The results of this experiment are illustrated in FIGS. 10*a* and 10*b*. Again, Test A illustrates that the differential pressure decay rate at the beginning and near the end of the test is similar to that illustrated in FIGS. 6*a*–6*c* with Example 1. Opening and closing the mouth caused the volume within the respirator cavity to change and the changes were recorded by the strip chart as a series of very sharp peaks and valleys. In Test B, during the first wide opening of the mouth. the seal broke and the strip chart recorder instantly recorded a very substantial pressure differential decay. The respirator then resealed itself, but continued to have a significant leak. Note that the effect of the seal breaking is instantly recorded.

EXPERIMENTAL EXAMPLE 5

In this experiment. an artificial leak was provided through a 15 mm long Tygon tube having an inside diameter of 0.050 inches and an outside diameter of 0.090 inches. There may have been some differentiation of the cross-sectional area of the flexible tubing. The Tygon tubing was manufactured by Norton Plastics.

Figure 11:
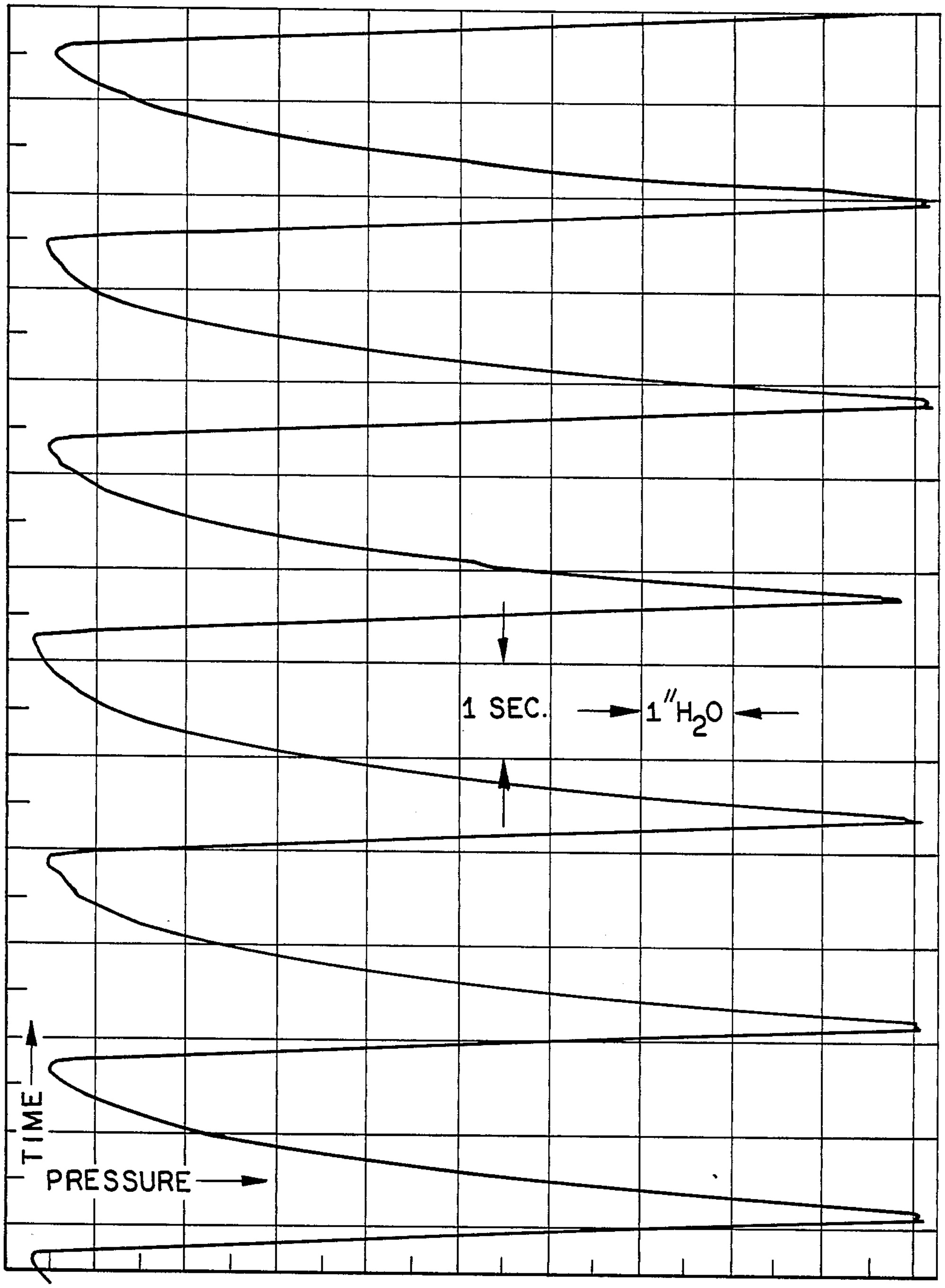
FIG. 11 is a graph of pressure versus time for a series of leakhole experiments with a half mask using an artificial leakhole of about 1.0 mm ID.
Figure 12:
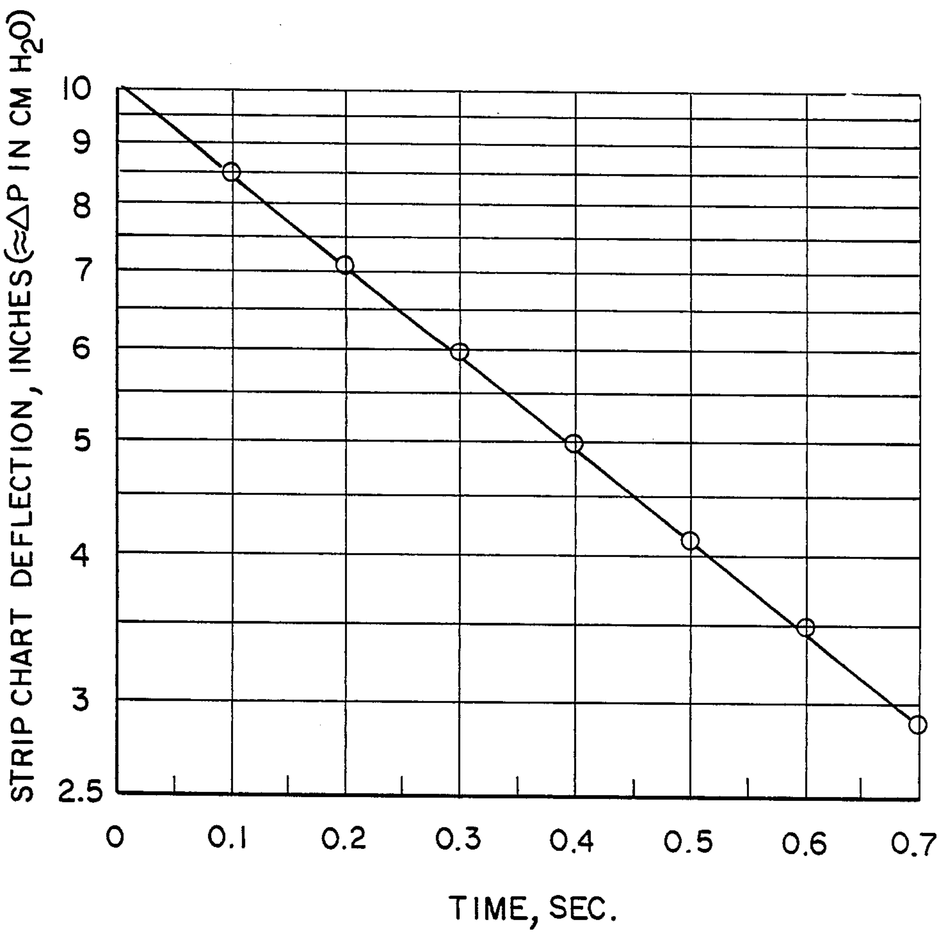
FIG. 12 is a log-linear plot of the change in pressure versus time of the bottommost leakhole experiment of FIG. 11 with the pressure being plotted on the logarithmic scale.

Each test was run with a strip chart speed of 1 second/inch which was the fastest speed available on the strip chart used. The tester wore the half mask described in Example 1 and inhaled to create a negative pressure inside the respirator cavity volume. The valve of the normal breathing tube was closed during this test and once a negative pressure was established inside the respirator cavity volume, the valve associated with the leakhole of known dimensions (the Tygon tube) was opened and the differential pressure versus time was recorded by the strip chart. The results of a series of these tests is illustrated by FIG. 11, with each individual test plotting a graph which looks substantially similar to the remaining tests. Accordingly, only one result was plotted on log-linear paper with the pressure differential being plotted on the log scale while the time was plotted on the linear scale. This plot, as illustrated in FIG. 12, produced a straight line having a specific slope which indicated that the leakage was steady, that is, the percentage of decay of the pressure differential per unit of time was constant. The graphs illustrated in FIGS. 11 and 12 represent the leakage in the face mask due to both the leakhole of known dimensions and to all the unknown leakages. The respirator volume cavity achieved substantial pressure equilization in approximately 0.7 sec. Consequently, the leakhole of known dimensions was significantly larger than the summation of all the leakages which occurred during the breath holding tests of Example 1 and illustrated by FIG. 7. In other words, the decay rate in FIG. 7 is much slower than the decay rate illustrated in FIG. 12. Consequently, the leakhole of known dimensions represents a leakage which was perhaps several magnitudes of order larger than the summation of the unknown leakages. Since the artificial leakhole was much larger than the summation of unknown leakages, the summation of the unknown leakages can be assumed to not affect the leakhole tests for volume determination. Consequently, FIG. 12 can be directly correlated with calibrated charts for the purposes of determining the respirator cavity volume.

Figure 13:
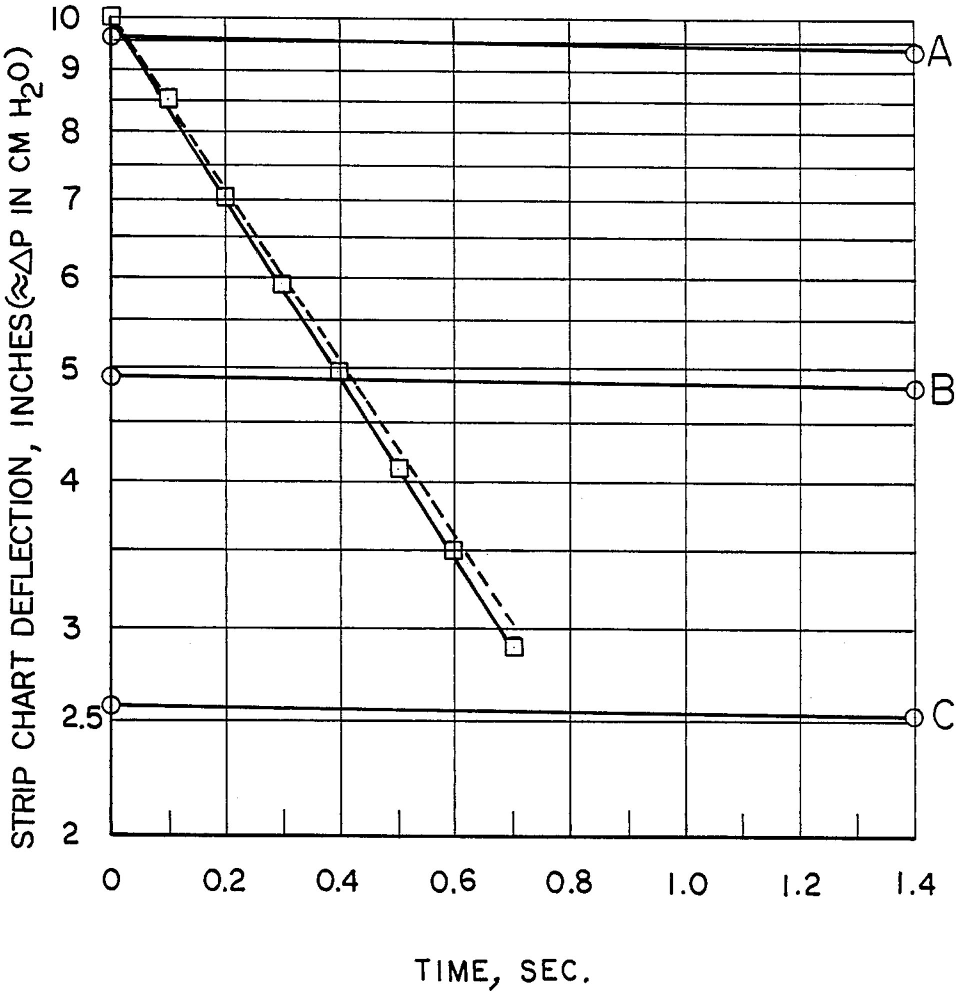
FIG. 13 is a log-linear graph of the change in pressure versus time of the plot of FIG. 7 superimposed upon the plot of the artificial leakhole test of FIG. 12 for the same time increment. Pressure decay due to the artificial hole leakage alone is shown by a dashed line.

If the artificial leakhole was not much larger than the summation of the unknown leakages, the plot of FIG. 2 could be used to determine the interior respirator cavity volume by merely subtracting the plot of the summation of the leakages for the mask as shown in FIG. 7. This is illustrated by FIG. 13 which illustrates curves A, B and C of FIG. 7, showing the pressure differential versus time over the time frame of 1.4 seconds. Superimposed upon each of these graphs is a solid line E which is the straight line shown in FIG. 12. The dotted line D adjacent the solid line E represents the pressure decay line due to the artificial leakhole alone, that is, it represents the subtraction of the summation of the unknown leakages from the slope of the line E representing both the summation of the unknown leakages and the artificial leakhole, as taken from FIG. 12.

EXPERIMENTAL EXAMPLE 6

Rather than using a half-mask as was done in all the previous examples, this experiment employs a Willson full face piece respirator Model BM 1423. This face mask, like the half mask used in Examples 1–5 includes two filter canisters. As explained in Example 1, one of the filter canisters was completely sealed while the other filter canister was transformed into a test canister with three inlet tubes formed and sealed onto the filter canister.

Figure 14C:
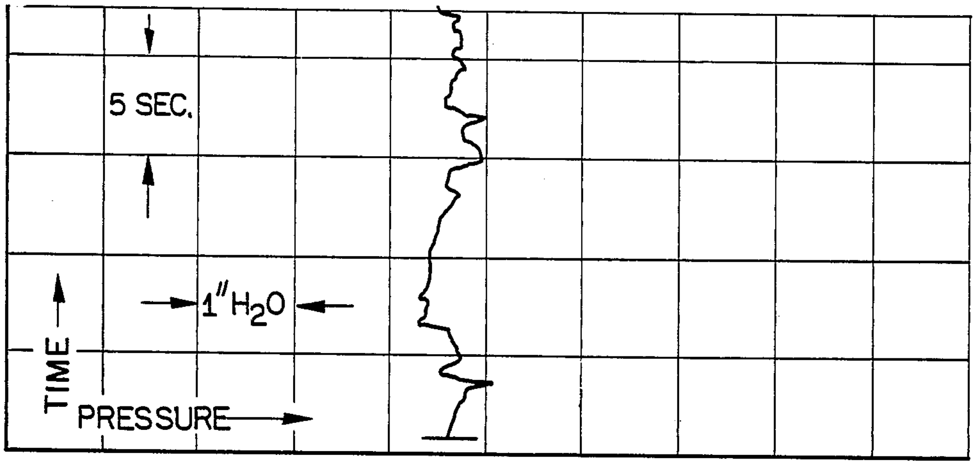
FIGS. 14*a*, 14*b* and 14*c* are strip chart graphs of pressure versus time illustrating three different breath-holding tests without body or face movement and with a full- face mask respirator.
Figure 14B:
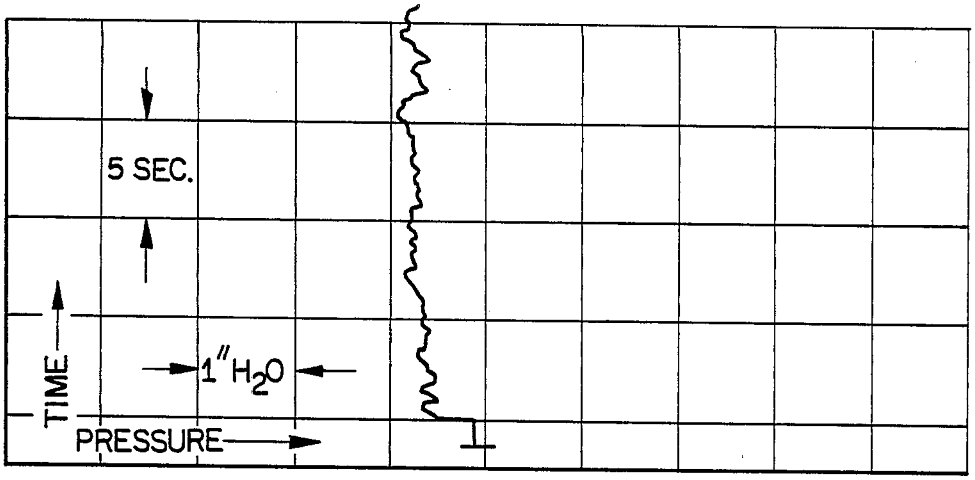
Figure 14A:
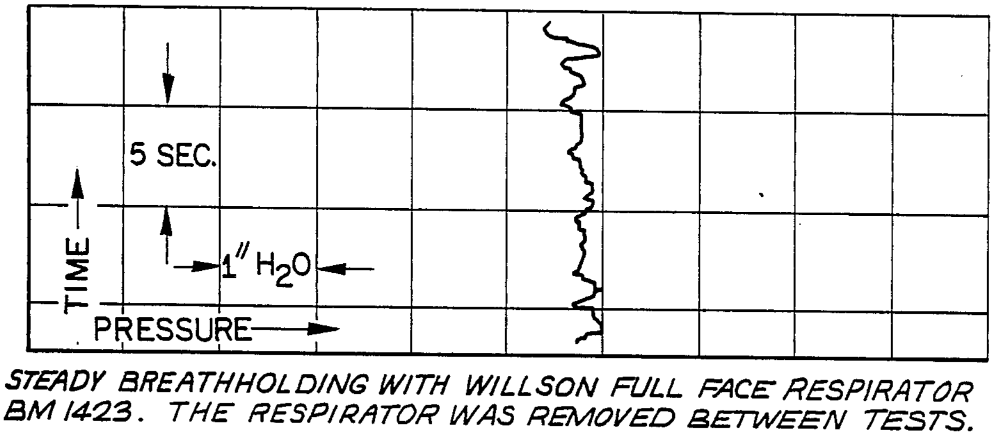

The breath holding experiments described in Example 1 were repeated in this experiment and, like the experiment described in Example 1, the head movements of the tester and the facial features remained steady throughout the experiment. Moreover, the experiment was performed in substantially the same manner, that is, the tester inhaled to create a negative pressure and held his breath for approximately 20 seconds for each test. Three experimental runs were conducted and labelled as A, B and C, as shown in FIGS 14*a*, 14*b* and 14*c*. In experimental run A, the pressure differential was greater than that of B and C. Although each of these experimental runs do not illustrate a line as linear as that shown in FIG. 6, each test does demonstrate an almost perfect seal with a slight overall steady decay rate in the pressure over a specified time.

EXPERIMENTAL EXAMPLE 7

Figure 15B:
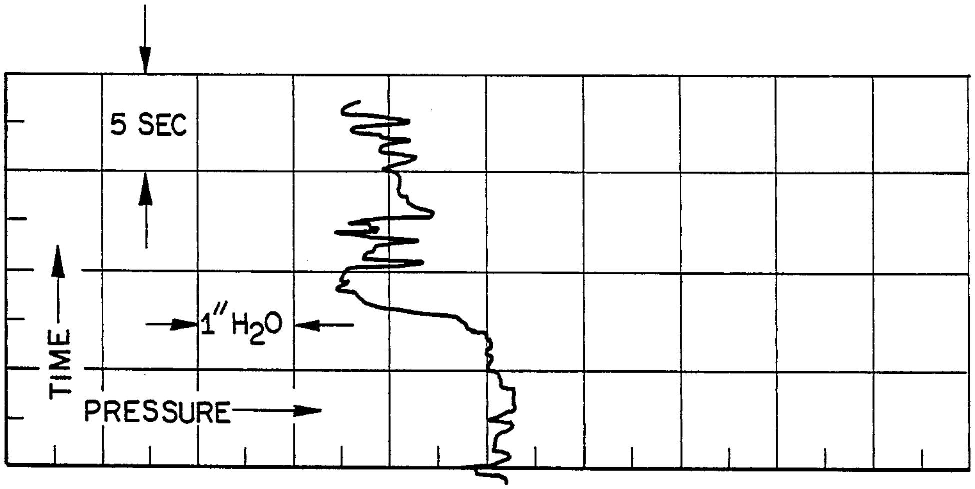
FIGS. 15*a* and 15*b* are linear-linear graphs of pressure versus time during two breath-holding tests using a full-face mask respirator while conducting up and down head movements during the tests.
Figure 15A:
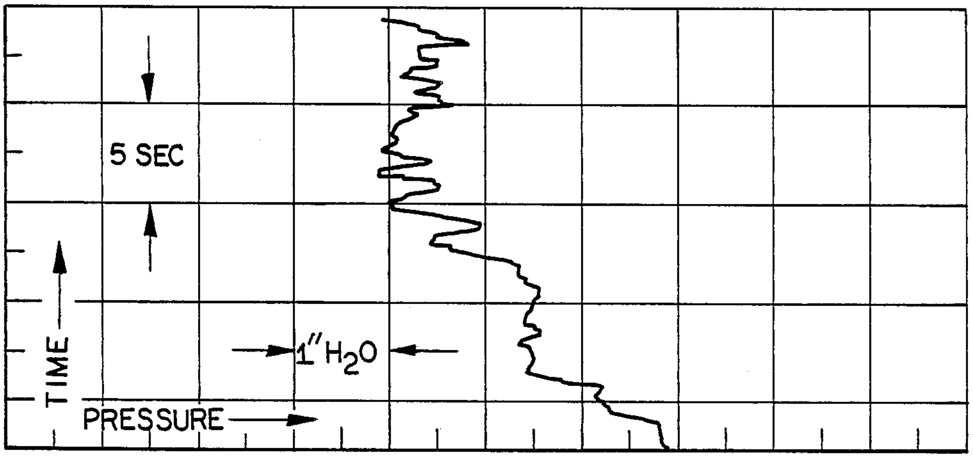

In this Example, the Willson full-face mask was employed. During the breath holding period, the tester performed the conventional up and down head movement. The strip chart results are demonstrated in FIGS. 15*a* and 15*b* for each experimental run A and B.

EXPERIMENTAL EXAMPLE 8

Figure 16B:
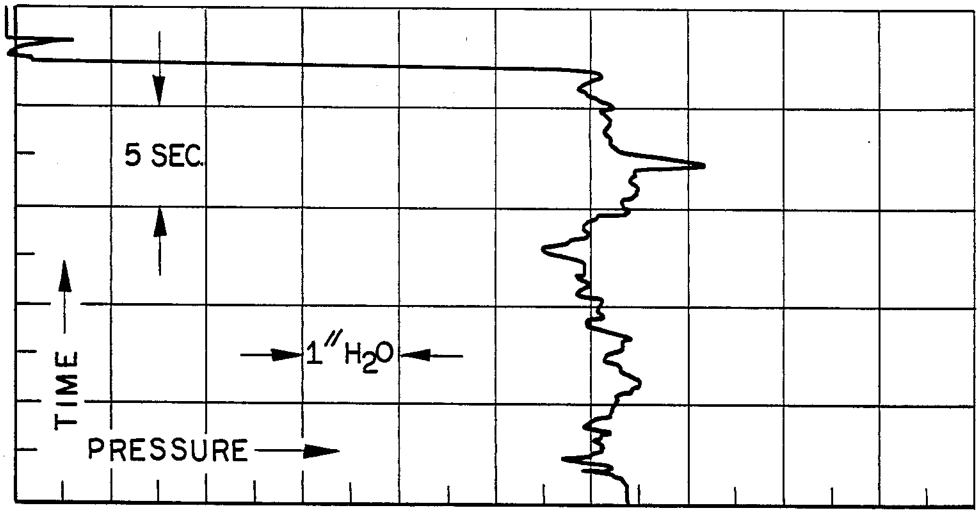
FIGS. 16*a* and 16*b* are linear-linear graphs of pressure versus time during two breath-holding tests using a full-face mask respirator while conducting side-to-side head movements during the tests.
Figure 16A:
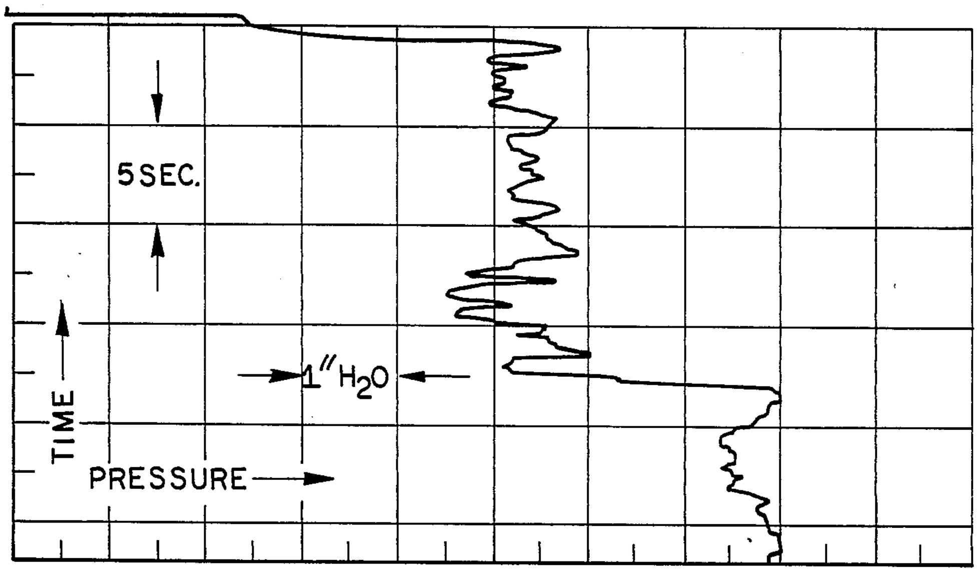

In this experiment, the Willson full-face mask was used. During the breath holding period, the tester moved his head in the conventional side-to-side manner. The results of this test are graphically illustrated in FIGS. 16*a* and 16*b* in experimental runs A and B. Experimental run B demonstrated an overall declining decay rate of the differential pressure over time. In experimental run A, the face mask apparently developed a leak during the side-to-side head movement and the overall pressure differential dropped. This was instantly recorded. After the face mask apparently became unsealed, it resealed itself and the overall decay rate continued at a rate approximately the same as before the mask became unsealed.

EXPERIMENTAL EXAMPLE 9

Figure 17C:
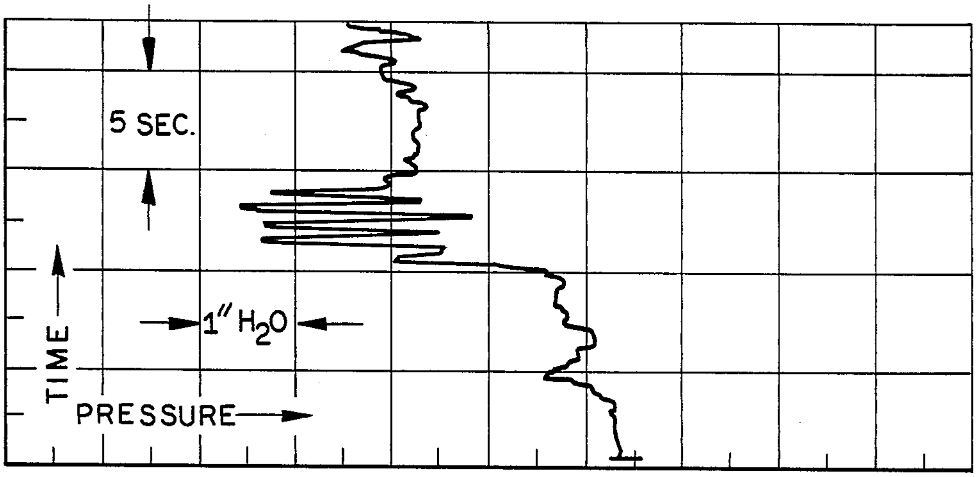
FIGS. 17*a*, 17*b* and 17*c* are graphs of pressure versus time during three breath-holding tests using a full-face respirator while conducting open and closed mouth movements without inhaling during the tests.
Figure 17B:
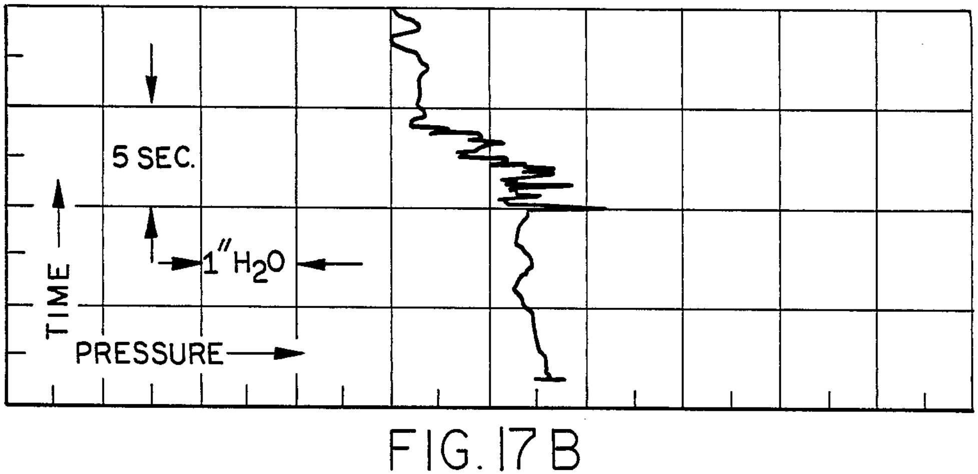
Figure 17A:
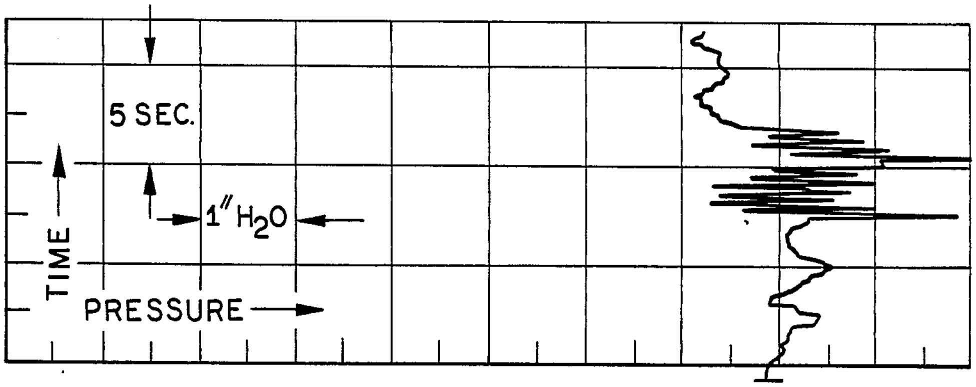

In this Example, the Willson full-face mask respirator was employed and during the breath holding test described in Example 1 the tester performed the open and close mouth exercise as described in Example 4. Experimental runs A, B and C were conducted. During the specific exercise, each run illustrated a series of sharply angled peaks and valleys. Both before and after the exercise the decay rate was substantially steady state as illustrated in FIGS. 17*a,* 17*b* and 17*c.*

EXPERIMENTAL EXAMPLE 10

Figure 18:
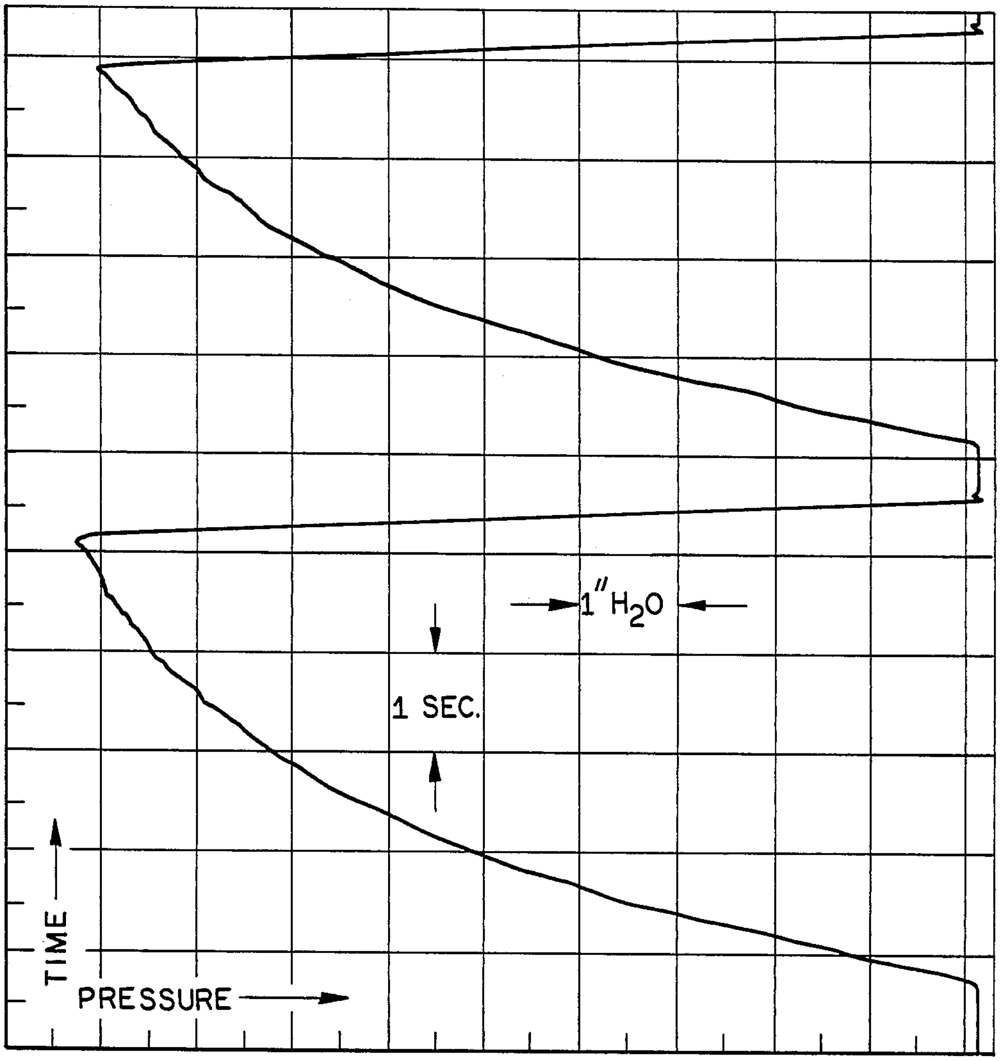
FIG. 18 is a linear-linear graph of the change in pressure versus time of two leakhole experiments with a full-face respirator having an artificial leakhole of about 1.0 mm ID.
Figure 19:
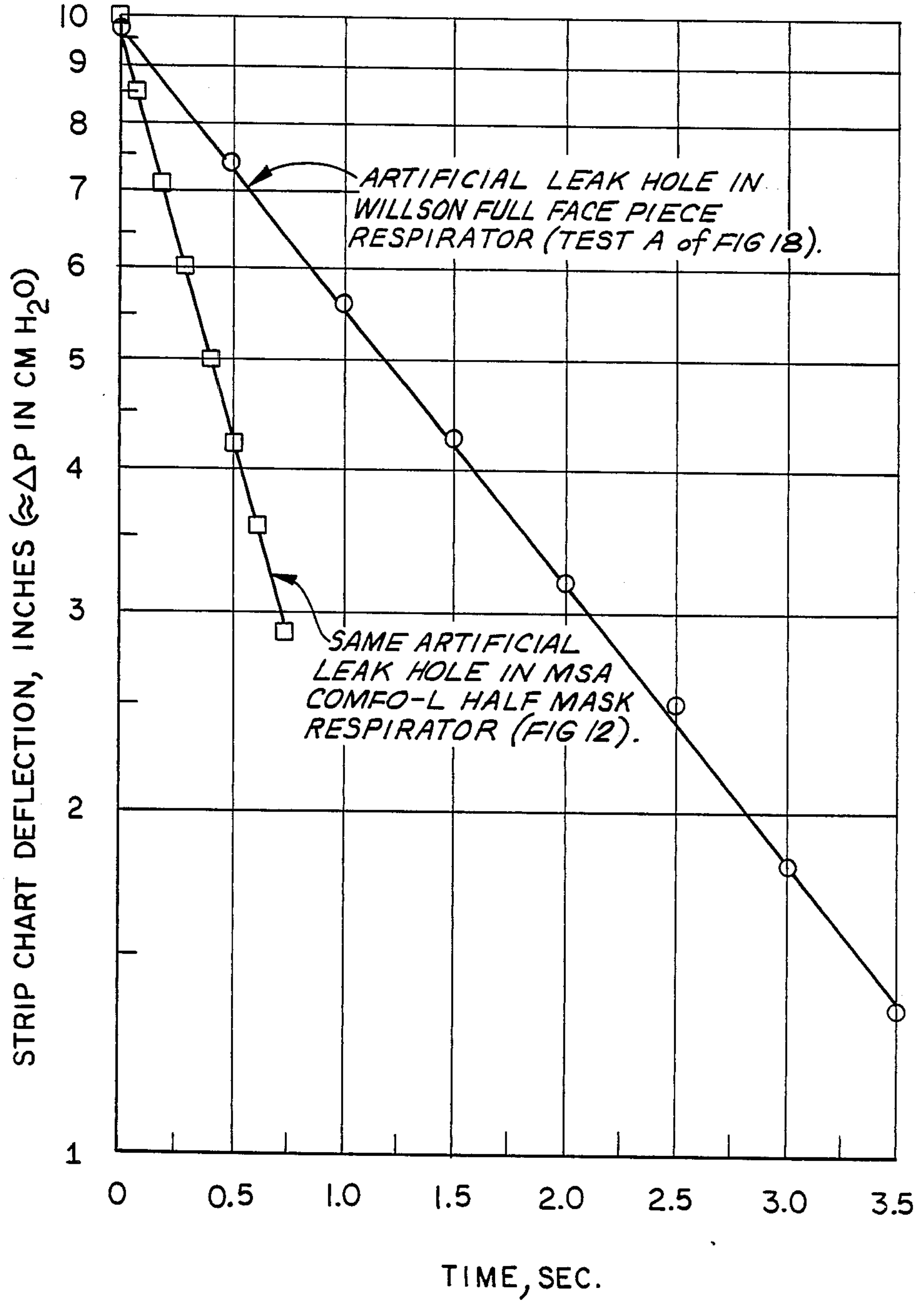
FIG. 19 is a log-linear plot of the change in pressure versus time of the leakhole test for a half mask versus full mask respirator taken from FIGS. 12 and 18 (Test A).

In this Example, the leakhole test described in Example 5 was performed on the Willson full-face mask respirator Model BM 1423. As described in Example 5, the artificial leakhole has an inside diameter of 0.050 inches or about 1.0 mm since the flexible tubing was possibly deformed. Both experimental runs A and B, as illustrated in FIG. 18, demonstrated a significantly longer decay rate for the large volume of the full face mask respirator, as compared to the half mask decay rate for the same hole as illustrated in FIG. 11. Accordingly, since the exponential curve shown in FIG. 18 illustrates a longer decay time, one would expect that a log-linear plot of the exponential curve of FIG. 18 would result in a line having a slope significantly less than the slope of the line shown in FIG. 12. In reality, this expected result occurred and is illustrated in FIG. 19 which shows the effect of leakage through the same size hole in two different respirator cavity volumes.

This Example proves the disadvantage of the Louisville Kentucky Metropolitan Sewer District method which was modified by Mr. Miller as explained in his presentation titled "The Development and Validation of Simple Respirator Fit Test," described previously. In other words, having a large respirator cavity volume when employing the method described by Mr. Miller would likely result in a full-face mask passing the test for proper fitness than would a small respirator cavity volume. This result would be true despite the fact that each mask could contain substantially the same amount of leakage.

EXPERIMENTAL EXAMPLE 11

In order to determine the cavity volume of the face mask respirator when employing the leakhole of known dimension test, a series of calibration curves were generated. In other words, a comparison between the slope shown in FIG. 12 and the slope of a series of calibration curves would result in an overall estimation of the internal respirator cavity volume for each type of mask commercially available.

Figure 21:
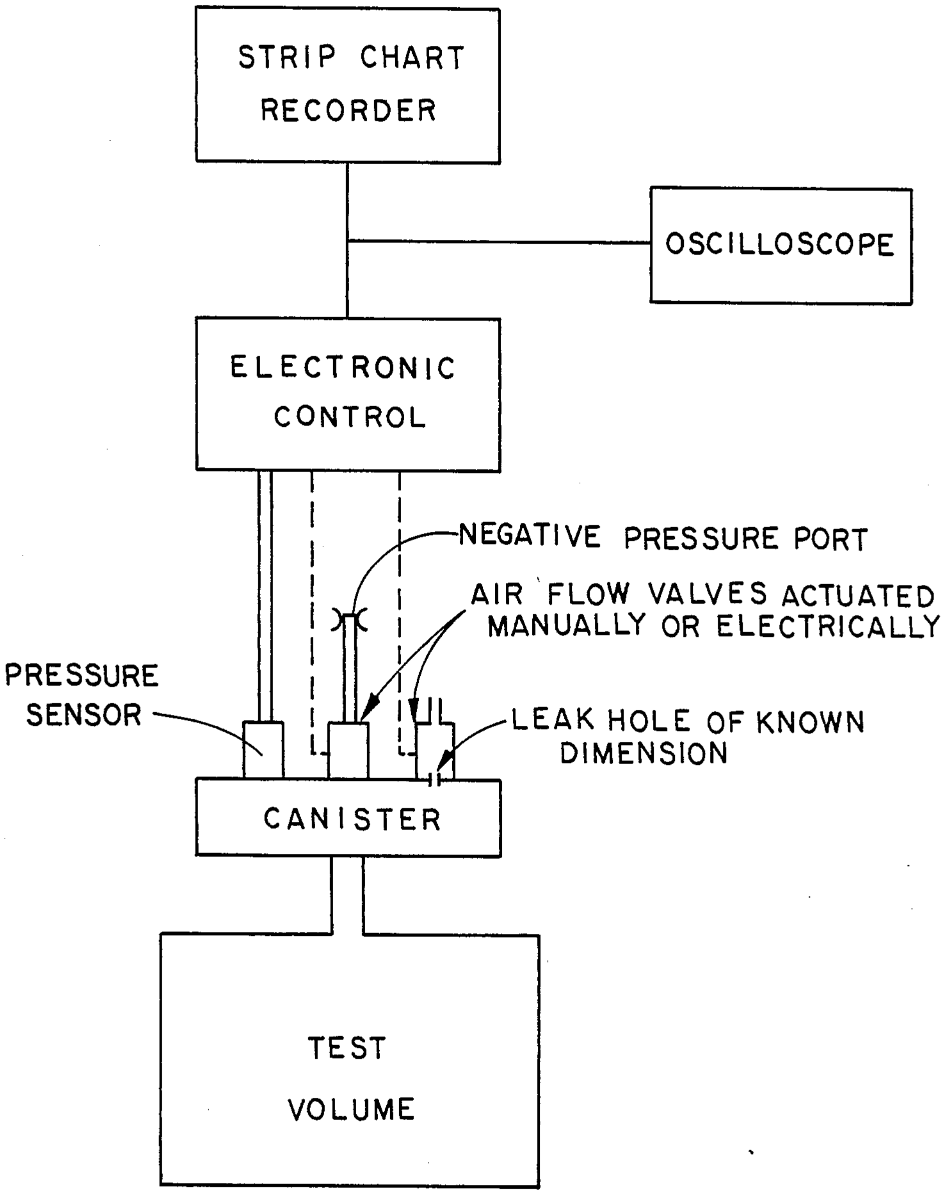
FIG. 21 is a schematic diagram illustrating the test equipment system employed for volume calibration with a specific size leakhole.

FIG. 21 illustrates schematically the equipment employed in generating a series of calibration curves or graphs. In this example, a known size test volume was connected to a pressure sensor as was described with respect to Example 1. Moreover, the pressure demodulator, oscilloscope and strip chart were connected to one another in the same manner described in Example 1. The test volume was also connected with a canister, which in turn was coupled with a pressure sensor, a negative pressure port and a leakhole of known dimension. The leakhole was Tygon tubing having an internal diameter of about 0.050 inches. Flow valves were fluidly coupled to the negative pressure port and to the leakhole. The flow valves were electrically actuted by an electronic control. The strip chart and oscilloscope were coupled with the electronic control.

In the first experimental run, a small fixed volume was employed. A differential pressure was created in the small fixed volume $V_1$ by closing the flow valve to the leakhole, opening the valve to the negative pressure port and employing a vacuum to evacuate the small fixed volume to a specific negative pressure. Once the negative pressure differential was created, the valve to the negative pressure port was closed and the valve for the leakhole of known dimension was opened so that the air leaked into the small known test volume through the leakhole. The results were recorded on the strip chart.

Figure 20:
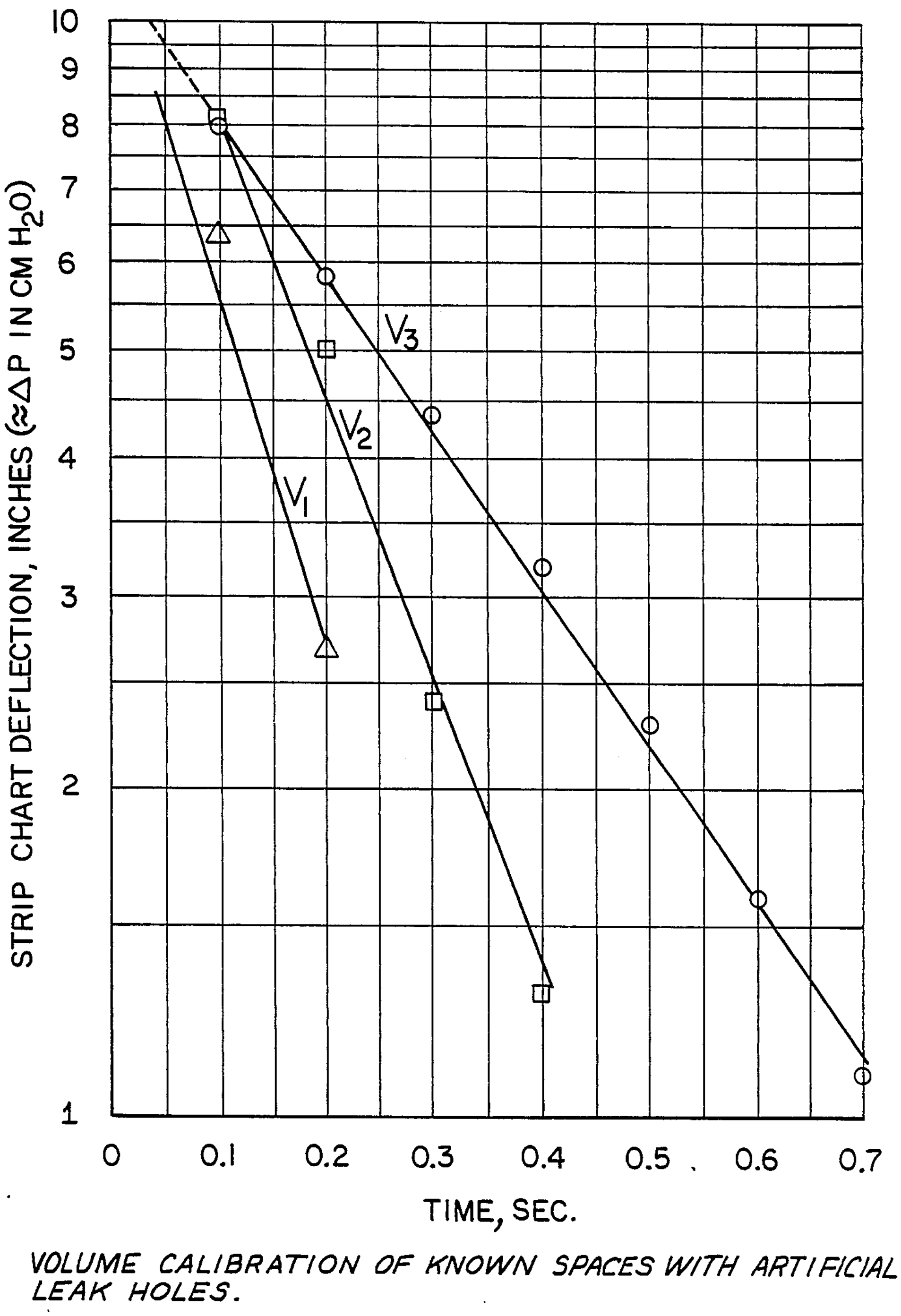
FIG. 20 is a log-linear plot of the pressure versus time of three different volumes, all having artificial leakages through the same size leak hole.

This test was repeated for a medium ($V_2$) and large test ($V_3$) volume of known size. FIG. 20 illustrates the results plotted on log-linear graph in which the differential pressure is plotted on the log scale and time is plotted on the linear scale. As one would expect, the leakhole can substantially equilibrate the pressure between the known test volume and the outside surroundings quicker for the $V_1$ volume than for the $V_3$ volume. For this reason, the slope of the line that represents the $V_1$ volume is steeper than the slope of the line that represents the $V_3$ volume. A comparison between a calibration chart having known volumes with the graph illustrated in FIG. 13 indicates the respirator cavity volume when worn by the tester.

In summary, recent studies have shown that in quantitative respirator fit testing with aerosols, complex and incomplete mixing of the aerosol occurs in the respirator cavity. Thus, the aerosol concentration sample obtained through the probe depends on the location of the aerosol probe relative to the nose and mouth inhalation and exhalation flow streams. Giving a leak of known rate at a specific location in the mask, the aerosol concentration measured with different masks differs considerably from each other. Generally, the location of leaks are not known, which adds further unknowns to the problem. A leak near the exhaust valve will contribute less aerosol than a leak from which the particles are carried toward the wearer's nose or mouth. While one may claim that the measurement should be made near the mouth or nose, conventional fit testing does not measure the inhaled or exhaled stream, but probes only in the area of the nose or mouth. While aerosols mix slowly, pressure can be assumed to equalize instantly. Thus, the effect of a leak anywhere in the respirator cavity is sensed instantly and the location of the pressure sensor is not critical, for example, it may be in the air supply hose for an air supplying respirator.

The present invention pressure test is a quantitative test and is an inexpensive alternative to the conventional quantitative fit tests using aerosols. The pressure test does not require the generation of an aerosol cloud and enclosure in a chamber, nor is it invasive. It does not require puncturing of the mask for a probe. Since the pressure can be sensed anywhere in the respirator cavity, such as in the air purifying element, this non-invasive technique permits quantitative fit testing of the actual respirator to be worn. It is also ideally suited for a quick check with the actual respirator before entering a hazardous environment.

Moreover, conventional face mask respirators can be adapted to include a pressure sensor in the filter canister, for example, or the face mask can have a pressure sensor molded into the body. Once the respirator cavity volume is determined for the specific wearer who will wear the mask, that data can easily be entered in a small calculator which can also be built into the conventional face mask. Then, the pressure sensor could provide the built-in calculator with the pressure whenever a negative pressure is created, such as by covering the filter canisters with the palms of one's hands, so that a fit factor could be calculated during use of the respirator. In this manner, the wearer would always be aware of the fit of the face mask while performing various chores in the working environment. Studies could determine fit factors for each type of face mask based upon the tests of the present invention and based upon different working environments. Accordingly, when a wearer observes a fit factor that is below his specific protection level, he can either reseat the face mask to obtain a better seal, or replace the face mask if it is worn.

Modification of the present invention may be made without departing from the spirit of it.

What is claimed is:

1. A non-invasive, quantitative method for fit testing a face mask respirator to an end user, comprising:

(1) donning a face mask respirator forming a respirator cavity of known volume with the face of an end user;
(2) sealing all known inlets into said face mask respirator;
(3) creating a negative pressure within said respirator cavity;
(4) recording the pressure within said respirator cavity with respect to time while a negative pressure exists within said cavity; and
(5) determining a non-dimensional quantitative fit factor based upon the recorded pressure change for the known respirator cavity volume for a specific period of time whereby to indicate the degree of protection provided by the face mask respirator to the end user, said quantitative fit factor being defined by $$\frac{1}{\frac{\text{Ln } P_1/P_2}{t_2 - t_1} \times t}$$

where
$P_1$=initial pressure in respirator cavity at time $t_1$
$P_2$=pressure in respirator cavity at time $t_2$
$t_1$=initial time
$t_2$=10 to 60 seconds after $t_1$
t=total time of negative pressure in respirator cavity (10 to 60 seconds), fixed for all determinations.

2. A non-invasive, quantitative method for determining the volume of a respirator cavity formed by a face mask respirator when worn by an end user, comprising:

(1) donning a face mask respirator forming a respirator cavity of unknown volume with the face of a end user and having a sealable leakhole of known dimensions communicating with said face mask respirator cavity;
(2) sealing all known inlets into said face mask respirator;
(3) creating a negative pressure within said respirator cavity;
(4) opening said leakhole and recording the pressure within said respirator cavity with respect to time while a negative pressure exists within said cavity; and
(5) determining the volume of said respirator cavity by plotting a graph of recorded pressure change versus time obtained by the step of recording the pressure with respect to time for said leakhole of known dimensions and comparing the slope of said pressure change to a series of slopes of known volumes on a calibration graph.

3. A non-invasive, quantitative method for fit testing a face mask respirator to an end user comprising:

(1) donning a face mask respirator forming a respirator cavity of unknown volume with the face of the end user, said respirator having a sealable leakhole of known dimensions communicating with said respirator cavity;
(2) sealing all known inlets into said respirator;
(3) creating a negative pressure within said respirator cavity;
(4) recording the pressure within said respirator cavity with respect to time while a negative pressure exists within said cavity;
(5) plotting a graph of recorded pressure change versus time obtained by the step of recording the pressure within said respirator cavity with respect to time and deetermining the slope of said pressure change;
(6) recreating a negative pressure within said respirator cavity;
(7) opening said leakhole and recording the pressure within said respirator cavity with respect to time while a negative pressure exists within said cavity and plotting a graph of recorded pressure change versus time;
(8) determining the volume of said respirator cavity when unknown leakages are not minor, by comparing the slope of said graph obtained by step (7) minus the slope of said graph obtained by step (5) to a series of slopes of known volume on a calibration graph, and by selecting the volume from said series of slopes which most closely approximate said slope obtained by step (7) minus said slope obtained by step (5); and
(9) determining a non-dimensional quantitative fit factor based upon recorded pressure change for the determined respirator cavity volume for a specific period of time whereby to indicate the degree of protection provided by the face mask respirator to the end user, said quantitative fit factor being defined by $$\frac{1}{\frac{\text{Ln } P_1/P_2}{t_2 - t_1} \times t}$$

where:
$P_1$=initial pressure in respirator cavity at time t.
$F_2$=pressure in respirator cavity at time $t_2$
$t_1$=initial time
$t_2$=10 to 60 seconds after $t_1$ t=total time of negative pressure in respirator cavity (10 to 60 seconds), fixed for all determinations.

4. The methof of claim 1, 2 or 3, wherein said negative pressure does not exceed the value at which said face mask respirator significantly deforms.

5. The method of claim 1, 2 or 3, wherein the step of sealing all known inlets comprises covering all known inlets with the palms of the hands of the user.

6. The method of claim 1, 2 or 3, wherein the step of creating a negative pressure within said respirator cavity includes inhaling by the user to obtain a negative pressure greater than 1 cm of water.

7. The method of claim 1, 2 or 3, wherein the step of recording the pressure within said respirator cavity with respect to time includes recording the pressure and time by analog or digital signals.

8. The method of claim 1, 2 or 3, wherein the step of donning said face mask respirator comprises donning a half-mask respirator, a quarter-mask respirator, a full face mask respirator, or a helmet-hood respirator.

9. The method of claim 1, 2 or 3, wherein the step of donning said face mask respirator comprises donning an air supplied respirator.

10. The method of claim 1 or 2 wherein said slope is defined by $$\frac{\mathrm{Ln}\ P_1/P_2}{t_2 - t_1}$$

where:

$P_1$=initial pressure in respirator cavity at time $t_1$ $P_1$ $P_2$=pressure in respirator cavity at time $t_2$ $t_1$=initial time $t_2$=10 to 60 seconds after $t_1$.

* * * * *

UNITED STATES PATENT AND TRADEMARK OFFICE

CERTIFICATE OF CORRECTION

PATENT NO. : 4,846,166

DATED : July 11, 1989

INVENTOR(S) : Klaus Willeke

It is certified that error appears in the above-identified patent and that said Letters Patent is hereby corrected as shown below:

Column 24, Line 33: "determining" is spelled incorrectly

Column 26, Line 6: "claim 1 or 2" should read "claim 2 or 3"

Column 26, Line 14: the "$P_1$" at the end of this line should be deleted

Signed and Sealed this

Fifteenth Day of May, 1990

*Attest:*

HARRY F. MANBECK, JR.

*Attesting Officer*

*Commissioner of Patents and Trademarks*